United States Patent [19]

Danho et al.

[11] Patent Number: 5,182,263
[45] Date of Patent: Jan. 26, 1993

[54] ANALOGS OF TYROSINE SULFATE OR TYROSINE PHOSPHATE CONTAINING PEPTIDES

[75] Inventors: Waleed Danho, Wayne; Jefferson W. Tilley, North Caldwell; Joseph Triscari, Bloomfield; Rolf Wagner, West Milford, all of N.J.

[73] Assignee: Hoffmann-La Roche Inc., Nutley, N.J.

[21] Appl. No.: 732,435

[22] Filed: Jul. 18, 1991

Related U.S. Application Data

[63] Continuation of Ser. No. 311,872, Feb. 21, 1989, abandoned, which is a continuation-in-part of Ser. No. 185,228, Apr. 25, 1988, abandoned.

[51] Int. Cl.$^5$ .................. C07K 7/06; A61K 37/02
[52] U.S. Cl. ..................... 514/16; 514/11; 514/12; 514/13; 514/16; 514/15; 514/17; 514/18; 530/317; 530/324; 530/325; 530/326; 530/327; 530/328; 530/329
[58] Field of Search ............ 530/324, 325, 326, 327, 530/328, 329, 330, 331, 303, 309; 514/3, 12, 13, 14, 15, 16, 17, 18; 560/37, 41; 562/442, 450, 458; 548/252

[56] References Cited

U.S. PATENT DOCUMENTS

3,705,140 12/1972 Bernardi et al. ............ 530/329
4,204,068 5/1980 Caldwell et al. ............ 548/313
4,530,836 7/1983 Yanaihara et al. ............ 530/329

FOREIGN PATENT DOCUMENTS

79284 2/1988 Australia .
0189305 7/1986 European Pat. Off. .
0226217 6/1987 European Pat. Off. .
2030140 4/1980 United Kingdom .

OTHER PUBLICATIONS

Yuki et al., Chem. Pharm. Bull 19(8), pp. 1664–1668 (1971).
Cleland, Journal of Organic Chemistry 34(3), pp. 744–747 (1969).
Caldwell et al., J.C.S. Perkin I, 2, pp. 495–505 (1980).
Rudinger, Peptide Hormones, Parsons (ed.), U Park Press, Baltimore, pp. 1–7, 1976.
Marseigne et al., J. Med. Chem. 32, pp. 445–449 (1989).
Wanner et al., J. Med. Chem. 23, pp. 85–87 (1980).
Bergeson et a051819290 l., Chem. Abstr. vol. 105, No. 209396q (1986).

*Primary Examiner*—Y. Christina Chan
*Attorney, Agent, or Firm*—George M. Gould; William H. Epstein; Bruce A. Pokras

[57] ABSTRACT

Analogs of Tyrosine Sulfate or Tyrosine Phosphate containing peptides, the novel intermediate compounds used in the preparation of these analogs, as well as a method for suppressing appetite in subjects by administering to the subject an effective amount of CCK analog wherein one or more of any Tyrosine Sulfate present is substituted with a radical of the invention.

30 Claims, No Drawings

ANALOGS OF TYROSINE SULFATE OR TYROSINE PHOSPHATE CONTAINING PEPTIDES

RELATED U.S. APPLICATION DATA

This is a continuation of application Ser. No. 07/311,872 filed Feb. 21, 1989, now abandoned, which is a continuation in-part of pending U.S. patent application Ser. No. 185,228 filed Apr. 25, 1988, abandoned.

BACKGROUND OF THE INVENTION

Peptides are ubiquitous biological molecules and have, in recent years, become the subject of extensive research and investigation. For example, the possibilities for utilizing natural biological substances, such as peptides, as therapeutics for various disease states is being aggressively explored.

Elucidation of the amino acid sequences of such peptides such as Growth Hormone, Growth Hormone Releasing Factor, or Cholecystokinin (CCK) has lead to advancements in the understanding of how these molecules work in treating various disorders. However, peptides suffer from rapid degradation upon exposure to the internal milieu often resulting in low bioavailability. It has been recently discovered that in many instances if the amino acid constituency of many naturally occurring peptides is altered by single or multiple amino acid substitutions at different sites, the analogs of the natural peptide may degrade less rapidly and hence exhibit greater bioavailability and efficacy.

For example, CCK is a family of peptide hormones which vary in length up to 58 amino acids. The sequence of CCK first discovered contained 33 amino acids. CCK as well as fragments thereof, such as CCK-8 and CCK-7, have been shown to have satiety-inducing effects when administered peripherally to animals. CCK-8 has the amino acid sequence:

```
26    27              28   29   30   31   32   33
Asp—Tyr(SO3H)—Met—Gly—Trp—Met—Asp—Phe—NH2.
```

CCK-7 lacks the 26-position amino acid Asp.

While CCK analogs are known to have satiety inducing effects, they exhibit low bioavailability and are poorly absorbed. Tyrosine sulfate containing peptides are well known to suffer loss of the sulfate moiety upon storage, particularly when in solution. This has led to the synthesis of various CCK analogs wherein the attempt to improve properties such as stability and bioavailability has been made. A multitude of CCK analogs with various amino acid substitutions have yielded compounds with altered properties which enhance their potential usefulness in human therapeutics.

The instant invention comprises analogs of Tyrosine Sulfate or Tyrosine Phosphate containing peptides. Examples of Tyrosine Sulfate containing peptides include peptides such as gastrin, cholecystokinin, platelet factor 4, or hirudin. Many Tyrosine Phosphate containing peptides are also known such as human insulin receptor, progesterone receptor, or Lipocortin-I. All of these peptides may yield analogs according to the instant invention.

For example, Tyrosine Sulfate occupies the 27 position amino acid of CCK or its shorter analogs such as CCK-7 and 8. When this Tyrosine Sulfate is substituted by a radical of the invention, the result is a CCK analog which may exhibit greater bioavailability, and hence may lend itself more readily to absorbtion following oral administration.

SUMMARY OF THE INVENTION

The instant invention comprises analogs of Tyrosine Sulfate or Tyrosine Phosphate containing peptides wherein one or more of any Tyrosine Sulfate or Tyrosine Phosphate groups is substituted with a radical of the formula:

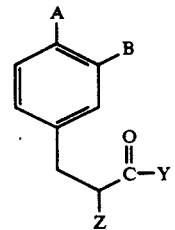

wherein A, B, Z, and Y are as described herein.

The instant invention also comprises the novel intermediate compounds used in the preparation of the radicals of the invention.

Preferred is where the analog is a Tyrosine Sulfate containing peptide wherein one or more Tyrosine Sulfate is substituted with a radical of the invention.

The instant invention also comprises a method of suppressing appetite in subjects by administering an appetite suppressing effective amount of a CCK analog wherein the Tyrosine Sulfate is substituted with a radical of the invention.

| DEFINITIONS | |
|---|---|
| 1. cyclic peptide | means a peptide where the omega carboxy terminus of one amino di-acid in the peptide chain is attached to the omega amino terminus of another di-amino acid in the peptide chain via the formation of an amide bond. The bonding between the two amino acids in the chain illustrated by the designation ⌊_____⌋ results in a ring structure. |
| 2. lower alkyl | means straight or branched chain saturated hydrocarbon containing from 1 to 7 carbon atoms. |
| 3. aryl | means substituted or unsubstituted phenyl or naphthyl wherein the substituents are one or more halogen, lower alkyl, lower alkoxy or nitro. |
| 4. lower alkoxy | means a lower alkyl ether group including but not limited to methoxy, ethoxy, propoxy, etc. |
| 5. lower alkenyl | means a straight or branched chain unsaturated hydrocarbon containing from 2 to 7 carbon atoms. |
| 6. Phe(3-COOH) | means the 3 position of the phenyl on phenylalanine is substituted with COOH. |
| 7. Phe(4-COOH) | means the 4 position on the phenyl of phenylalanine is substituted with COOH. |
| 8. Phe(4-CH2COOH) | means the 4 position on the phenyl of phenylalanine is substituted with CH2COOH. |
| 9. Phe(4-CH2COOC2H5) | means the 4 position on the |

-continued

| | DEFINITIONS |
|---|---|
| | phenyl of phenylalanine is substituted with $CH_2COOC_2H_5$. |
| 10. Phe(4-$CH_2CH_2COOH$) | means the 4 position on the phenyl of phenylalanine is substituted with $CH_2CH_2COOH$. |
| 11. Phe(4-$CF_2COOH$) | means the 4 position on the phenyl of phenylalanine is substituted with $CF_2COOH$. |
| 12. Phe(4-tetrazole) | means the 4 position on the phenyl of phenylalanine is substituted with a 5-tetrazoyl group. |
| 13. Phe(4-$CH_2$tetrazole) | means that 4 position on the phenyl of phenylalanine is substituted with a $CH_2$-[tetrazoyl] group. |
| 14. peptide | means a linear or cyclic peptide. |
| 15. Ac | means acetyl. |
| 16. (D,L), (D), or (L) | preceding the amino acid designation means that this amino acid exists in that specific isomeric form. i.e. (D,L)Phe means that the amino acid phenylalanine exists as a racemic mixture; (D)Phe means that the amino acid Phenylalanine exists as the R* stereoisomer; (L)Phe means that the amino acid Phe exists as the L stereoisomer or implied S configuration. All amino acids are represented by their commonly understood three letter designations. |
| 17. Compounds | where this term is used it includes enantiomers and racemates of the compounds. |
| 18. Tyrosine Sulfate | means the amino acid Tyrosine wherein a sulfate ester is present on the 4-position of the aromatic ring. |
| 19. Tyrosine Phosphate | means the amino acid Tyrosine wherein a phosphate ester is present on the 4-position of the aromatic ring. |
| 20. Desamino | means an amino acid which lacks the alpha-amino functional group. For example, in the context of the instant invention "Desamino Phe" means that the Phenylalanine lacks the alpha amino functional group which is defined by Z $$\overset{O}{\underset{\|}{(NH_2, NHCR_3, \text{etc.})}}$$ |
| 21.  | means a tetrazole wherein the functional group $R_2$ is attached to the 1 or 2 position nitrogen. |

DETAILED DESCRIPTION

The instant invention comprises analogs of Tyrosine Sulfate or Tyrosine Phosphate containing peptides wherein one or more Tyrosine Sulfate or Tyrosine Phosphate is substituted with a radical of the formula

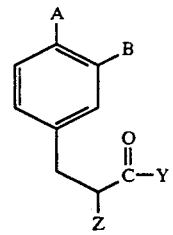

wherein one of A or B is selected from the group consisting of:

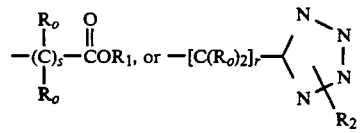

and the other of A or B is H;

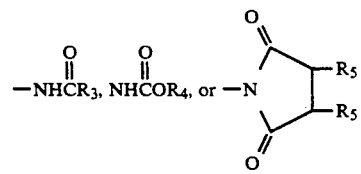

wherein X is another amino acid whose carboxy terminus is bound to the amino group.

and Y is H, OH, alkoxy, $NH_2$, or another amino acid whose amino terminus is bound to the carboxy group.

$R_0$ is: H, or F $R_1$ is: H, substituted or unsubstituted lower alkyl with the substituents selected from the group consisting of hydroxy, halogen, or aryl, $R_2$ is: H, lower alkenyl, substituted or unsubstituted lower alkyl with the substituents selected from 1 to 3 aryl groups.

$R_3$ is: H, lower alkyl, alkyl substituted by one or two aryl groups, or aryl $R_4$ is: lower alkyl, alkyl substituted by one or two aryl groups $R_5$ is: each independently H, lower alkyl, or taken together may form a six membered ring which may be aromatic.

s is: 0–2 r is: 0–2 with the proviso that if Z is other than NHX then Y is another amino acid whose amino terminus is bound to the carboxy group; or if Y is H, OH, alkoxy, or $NH_2$ then Z is NHX.

Preferred is an analog of a Tyrosine Sulfate containing peptide wherein one or more Tyrosine Sulfates are substituted with the radical of Formula I.

Preferred is an analog of CCK wherein the Tyrosine Sulfate is substituted with a radical of Formula I, wherein Z in Formula I is H or $$-\underset{\|}{\overset{O}{NHCR_3}}$$

with $R_3$ = lower alkyl or H.

Further preferred is wherein one of A or B in Formula I

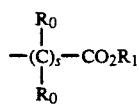

and the other of A or B is H.
Further preferred is where A in Formula I is

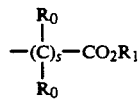

and B in Formula I is H.
More preferred are analogs of CCK wherein the Tyrosine Sulfate is substituted with the radical of Formula I wherein s is 1, $R_0$ is H or F, and $R_1$ is H.
Most preferred are analogs wherein $R_0$ in Formula I is H, yielding the preferred analogs of the formula:

Ac—(D)Phe(4-CH$_2$COOH)—Met—Gly—Trp—Met—Asp—Phe—NH$_2$
Ac—Phe(4-CH$_2$COOH)—Met—Gly—Trp—Met—Asp—Phe—NH$_2$

Ac—(D,L)Phe(4-CH$_2$COOH)—Lys—Gly—Trp—Met—Asp—N—methyl—Phe—NH$_2$

Desamino Phe(4-CH$_2$COOH)—Met—Gly—Trp—Met—Asp—Phe—NH$_2$
Desamino Phe(4-CH$_2$COOH)—Nle—Gly—Trp—Nle—Asp—N—methyl—Phe—NH$_2$ Also preferred are analogs wherein s in Formula I is 1, $R_0$ in Formula I is H, and $R_1$ in Formula I is CH$_2$CH$_3$ yielding preferred analogs of the formula:

Ac—(D)Phe(4-CH$_2$COOC$_2$H$_5$)—Met—Gly—Trp—Met—Asp (COOC$_2$H$_5$)—Phe—NH$_2$

Ac—Phe(4-CH$_2$COOC$_2$H$_5$)—Met—Gly—Trp—Met—Asp (COOC$_2$H$_5$)—Phe—NH$_2$

Also preferred are analogs wherein B in Formula I is

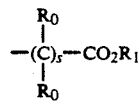

and A in Formula I is H.
More preferred are analogs wherein s in Formula I is 1 and $R_1$ in Formula I is H.
Most preferred is the analog of the formula:

Ac—(D,L)Phe(3-CH$_2$COOH)—Met—Gly—Trp—Met—Asp—Phe—NH$_2$

Also preferred is an analog of CCK wherein the Tyrosine Sulfate is substituted with a radical of Formula I wherein one of A or B in Formula I is

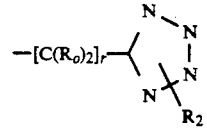

and the other of A or B in Formula I is H.
Further preferred is wherein A in Formula I is

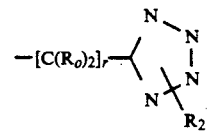

and B in Formula I is H.
Most preferred is wherein r in Formula I is 0 and $R_2$ in Formula I is H yielding the preferred analogs of the formula:

Ac—Phe(4-tetrazole)—Met—Gly—Trp—Met—Asp—Phe—NH$_2$
Desamino—Phe(4-tetrazole)—Met—Gly—Trp—Met—Asp—Phe—NH$_2$ Desamino—Phe(4-tetrazole)—Lys—Gly—Trp—Met—Asp—N—methyl—Phe—NH$_2$ Ac—(D,L)Phe(4-tetrazole)—Lys—Gly—Trp—Met—Asp—N—methyl—Phe—NH$_2$ Also preferred are analogs containing the radical of Formula I wherein r in Formula I is 1 and $R_2$ in Formula I is H yielding preferred analog of the formula:

Ac—(D)Phe(4-CH$_2$—tetrazole)—Met—Gly—Trp—Met—Asp—Phe—NH$_2$
Ac—Phe(4-CH$_2$—tetrazole)—Met—Gly—Trp—Met—Asp—Phe—NH$_2$
Ac—(D)Phe(4-CH$_2$—tetrazole)—Nle—Gly—Trp—Nle—Asp—N—methyl—Phe—NH$_2$
Ac—Phe(4-CH$_2$—tetrazole)—Nle—Gly—Trp—Nle—Asp—N—methyl—Phe—NH$_2$
Desamino—Phe(4-CH$_2$—tetrazole)—Nle—Gly—Trp—Nle—Asp—N—methyl—Phe—NH$_2$ The radicals incorporated into the analogs of Tyrosine Sulfate or Tyrosine Phosphate containing peptides according to the invention may be synthesized as follows:

Scheme I

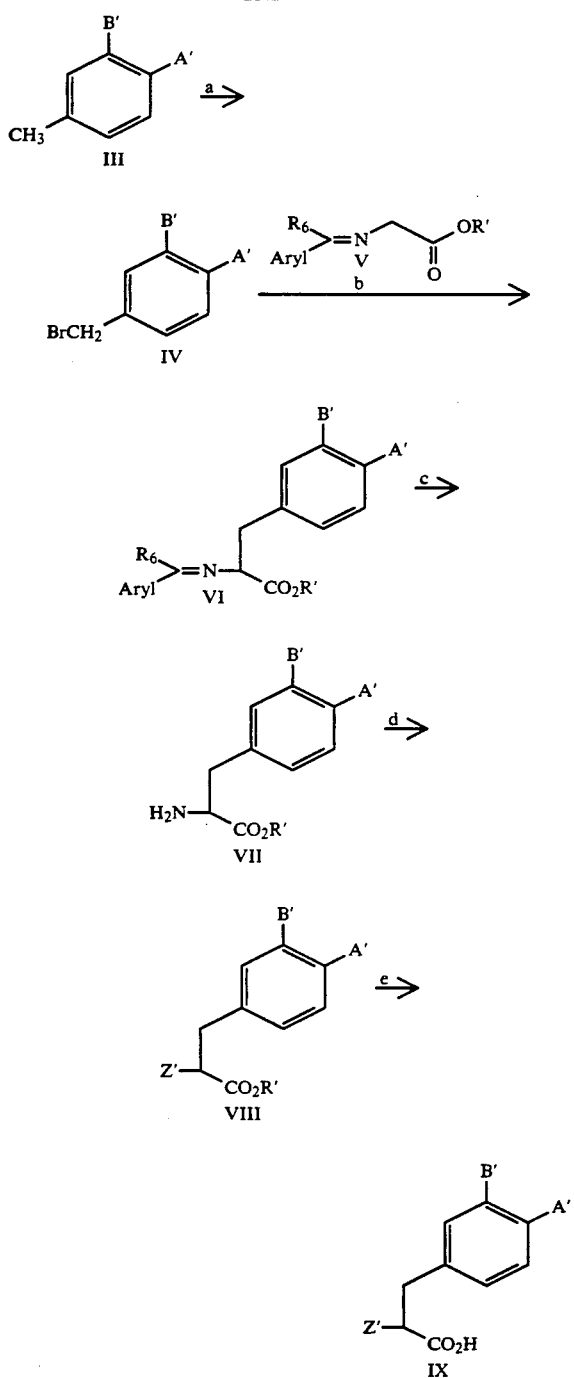

In Reaction Scheme I A' and B' are identical with A and B in Formula I with the proviso that $R_1$ and $R_2$ are not H.

R' may be a substituted or unsubstituted lower alkyl with the substituents selected from the group consisting of hydroxy, halogen, or aryl; or any suitable protecting group chosen so as to be easily removed selectively without affecting $R_1$, $R_2$ or Z' in step (e).

$R^6$ may be H or aryl, and Z' is $NH_2$, NHX,

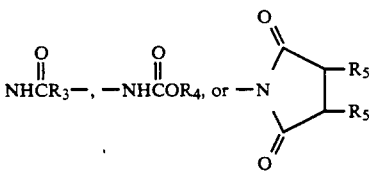

In Reaction Scheme I the formula III compound is reacted in step (a) with a halogenating agent dissolved in a nonpolar inert organic solvent which contains a catalytic quantity of a radical initiator at a temperature ranging from 60° C. to 80° C. until most of the formula III compound is consumed. A suitable halogenating agent is N-bromosuccinimide, a suitable nonpolar inert organic solvent is carbon tetrachloride, and a suitable catalytic radical initiator is azobisisobutyronitrile or benzoyl peroxide. The resulting formula IV compound can then be isolated by conventional methods such as chromatography or distillation. In step (b) the formula IV compound is reacted at about room temperature with a formula V compound wherein $R_6$ is aryl, in a biphasic mixture of, for example, methylene chloride and water which contains an inorganic base, such as alkali metal hydroxide and a phase transfer catalyst, such as a tetraalkylammonium salt. See the procedure described in O'Donnell, et al., *Tetrahedron Letters*, 2641 (1978). The resulting formula VI compound can be isolated by conventional methods, such as chromatography or can be used directly in step (c).

Alternatively, the formula V compound wherein $R_6$ is H, or aryl, can be deprotonated below room temperature with a suitable strong base, such as lithium diisopropyl amide or potassium hexamethyldisilazide, in an inert ethereal solvent, such as diethyl ether, tetrahydrofuran or dimethoxyethane to which is added a metal coordinating agent such as hexamethylphosphoric triamide. A solution of a formula IV compound in an ethereal solvent such as diethyl ether, tetrahydrofuran or dimethoxyethane, can then be added to the mixture preferably at a reaction temperature of about −78° C. After complete reaction and aqueous workup, the resulting formula VI compound may be isolated by conventional methods or may be used directly in step (c).

In step (c) the compound of formula VI is treated with at least one equivalent of a strong acid dissolved in a suitable organic solvent which contains excess water. Suitable acids are toluenesulfonic acid or hydrochloric acid, and tetrahydrofuran, ether or acetonitrile are suitable solvents. After complete reaction, the resultant compound of formula VII can be isolated as its salt by conventional methods such recrystallization or may be used directly in step (d), wherein the formula VII compound is treated with an acylating agent, such as acetic anhydride or t-butylpyrocarbonate, in the presence of a base which may be a tertiary amine such as triethyl amine; at a temperature ranging from 0° C. to room temperature. The choice of solvent is not critical for this reaction and is normally based on considerations of solubility and reactivity of the reaction components. Dichloromethane is useful for laboratory scale preparations. Isolation of the resulting formula VIII compound can be accomplished using conventional methods.

In step (e), the conversion of the formula VIII compound to a formula IX compound is carried out by selective ester hydrolysis. Appropriate conditions for this hydrolysis depend on the particular choice of R', $R_1$, $R_2$ and $Z'$ in the compound of formula VIII. Optimally, these groups are chosen so as to facilitate the selective conversion of $R'$ to hydrogen without affecting $R_1$, $R_2$ or $Z'$ using methods known in the art. For example, where $R'$ is mono- or diarylmethyl group it can be removed through treatment with hydrogen gas at atmospheric pressure in a polar organic solvent such as ethanol in the presence of a noble metal catalyst such as 10% Pd/C. These reaction conditions may be controlled so as not to affect $R_1$, or $R_2$ when these groups are lower alkyl, mono-, di-, or trihaloalkyl, or trialkylsilylalkyl and will not affect $Z'$ when $R_3$ and $R_4$ are appropriately selected, for example lower alkyl. The resulting Formula IX compound can be isolated by conventional methods.

Alternatively, when $R'$ is a small alkyl group such as methyl and $R_1$ is a bulky alkyl group such as a tertiary butyl group; selective base hydrolysis may be effected by treatment of the formula VIII compound with an alkali metal hydroxide, in the presence of a polar solvent until hydrolysis of $R'$ is complete. When done carefully these reaction conditions will not affect $R_1$, $R_2$ or $Z'$. Isolation of the formula IX compound can then be accomplished using conventional methods.

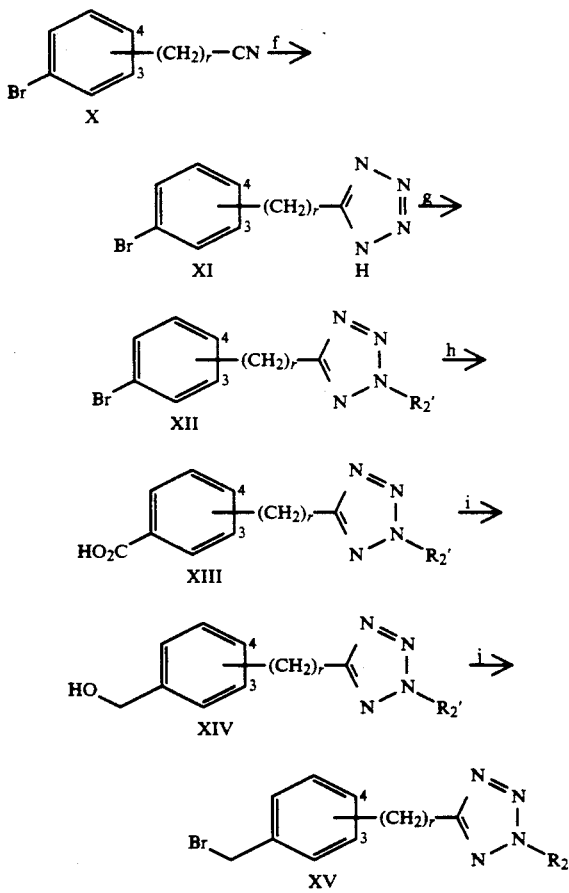

In Reaction Scheme II, r and $R'_2$ are as defined in Formula I for r and $R_2$ respectively except that $R'_2$ should not be H, and the side chain may be attached to either position 3 or 4 on the aromatic ring as indicated. In step (f) the formula X compound is treated with sodium azide and ammonium chloride in a polar aprotic solvent such as dimethylformamide at a temperature of about 90°–100° C. The resultant formula XI compound can then be isolated by conventional techniques. In step (g) the tetrazole of formula XI is treated with an excess of an alcohol capable of forming a stabilized carbonium ion in the presence of a strong acid (such as trifluoroacetic acid), at about room temperature. The major product from this process will be a formula XII compound, however, the regioisomer resulting from alkylation at N-1 of the tetrazole will also be formed in varying amounts depending on the selection of r and the particular reaction conditions. Formula XII compounds and their regioisomers may be separated but this is generally not necessary as both isomers will yield the same product when $R_2$ is converted to hydrogen. Alternatively, a primary or secondary alcohol can be reacted with a formula XI compound in the presence of a dialkyl azodicarboxylate and a phosphine in an inert solvent according to the procedure described by O. Mitsunobu Synthesis, (1981) 1; to give a formula XII compound, wherein $R'_2$ is derived from a primary or secondary alcohol.

In step (h) the formula XII compound is carbonylated according to the method of Schoenberg, et al. J. Org. Chem., 43 (1974), 3318. Thus a compound of formula XII is maintained under an atmosphere of carbon monoxide ranging from 100–200 psi in the presence of a tertiary amine base in a polar solvent system that contains a trialkyl or triaryl phosphine and a source of catalytic palladium zero. This mixture is maintained at about 100° C. from 1 to 3 days. The resulting formula XIII compound may be isolated by conventional techniques.

In step (i) the formula XIII compound is treated with a metal hydride reducing agent in an inert solvent at room temperature. The resulting compound of formula XIV compound may be isolated by conventional techniques. In step (j) the formula XIV alcohol is treated with triphenylphosphine and carbon tetrabromide in an inert solvent at or below room temperature, preferably at about 0° C. The resulting formula XV compound can be isolated by conventional means.

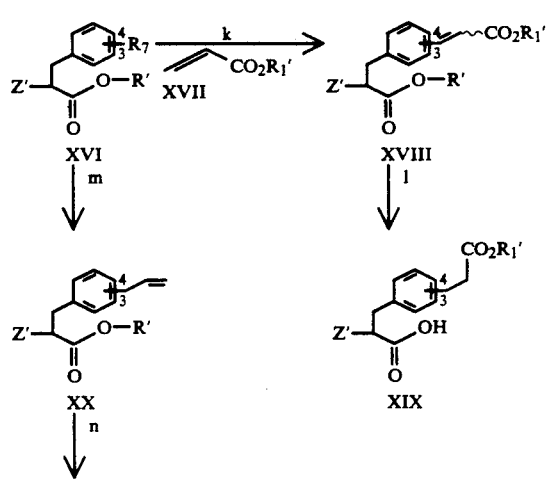

Scheme III -continued

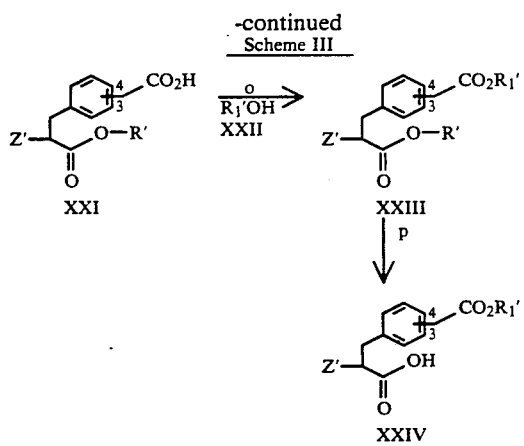

In Reaction Scheme III, R' is as previously defined, Z' is H, lower alkyl,

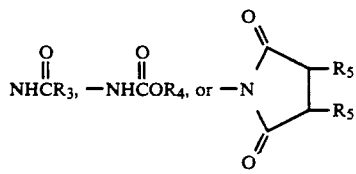

and $R_7$ is bromide, iodide, or a perfluoroalkylsulfonate ester which may be attached to the phenyl at either position 3 or 4 as set forth in formula XVI, and $R'_1$ is the same as $R_1$ in Formula I with the proviso that $R'_1$ is other than H. In step (k) the formula XVI compound is reacted with an acrylate of formula XVII in the presence of a source of palladium zero and a tertiary amine base. When $R_7$ is a perfluoroalkylsulfonate ester, this procedure is carried out in a polar aprotic solvent at a reaction temperature of 70°–100° C. as described by Chen et al., *Tetrahedron Letters*, 27, (1986) 1171. When $R_7$ is bromide or iodide, the reaction can be carried out as described by Heck, *Organic Reactions*, 27, (1982) 345. The side chain of the resulting formula XVIII compound becomes attached to the site of the departing $R_7$. The formula XVIII compounds may be isolated by conventional means.

Step (l) can be carried out in one or two steps depending on the particular choice of $R_1'$ and R'. When R' is mono- or diarylmethyl and $R_1'$ is lower alkyl, halo-substituted alkyl, or hydroxy substituted alkyl, and Z' does not contain a mono-, di- or triarylmethoxy group, catalytic hydrogenation over a noble metal catalyst, in a polar solvent at a hydrogen pressure of from one to three atmospheres results in the simultaneous reduction of the double bond and hydrogenolysis of the R' group yielding a formula XIX compound after a suitable isolation procedure. Alternatively, when R' is methyl or ethyl and $R_1'$ is a bulky substituent such as, tertiary butyl, catalytic hydrogenolysis may be carried out as above, and a separate selective hydrolysis step may be carried out as described above for step (e) in Scheme I to yield the formula XIX compound.

In step (m) the formula XVI compound where $R_7$ is perfluoroalkylsulfonate ester is treated with an alkyl trialkylstannane, a source of palladium zero, and an excess of lithium chloride in a polar aprotic solvent at about 90° C. The resulting formula XX compound can be isolated by conventional techniques. In step (n) the formula XX compound is reacted with a suitable oxidizing agent and a catalytic amount of ruthenium trichloride in a two phase system as described by Carlsen et al., *J. Organic Chemistry*, 46, (1981), 3936. Depending on the particular choice of reaction conditions this process may lead either directly to a compound of formula XXI or to an intermediate aldehyde which may be oxidized to a formula XXI compound according to the procedure described by Bal et al., *Tetrahedron*, 37, (1981) 2091. The resulting formula XXI compounds can be isolated by conventional techniques.

In step (o), an acid of formula XXI is converted to an ester of formula XXIII. The choice of $R_1'$ should be such that it will survive the reaction conditions required to generate an acid of formula XXIV and will thus depend on the selection of R' in the formula XXI compound. The formula XXI compound can be reacted with an alcohol of formula XXII in the presence of a coupling reagent and a catalyst in an inert solvent. Alternatively the formula XXI compound may be reacted with a dimethylformamide dialkoxyacetal in a inert solvent at a reaction temperature ranging from 60° to 80° C. The resulting formula XXIII compound can be isolated by convention means.

In step (p) the formula XXIII compound is converted to the formula XXIV compound as described in step (e) of Scheme I.

Scheme IV

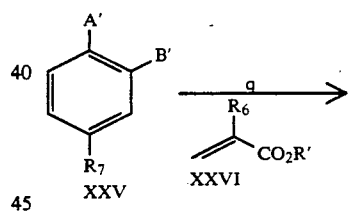

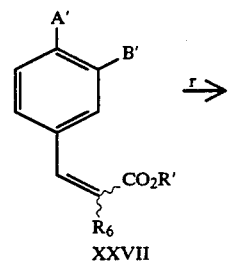

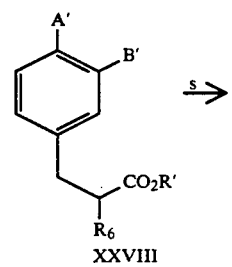

-continued
Scheme IV

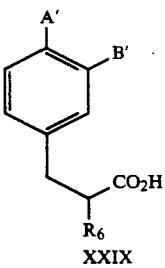

XXIX

In Reaction Scheme IV, A', B', $R_7$ and R' are as previously defined and $R_8$ is hydrogen or lower alkyl.

The compound of formula XXV can be prepared by known methods. In Step q the Formula XXV compound is treated with a compound of formula XXVI under the general conditions described for step k in Scheme III to give a compound of formula XXVII which can be isolated by conventional means. In step (r) formula XXVII compound is reduced to a formula XXVIII compound. When A' and B' contain groups resistant to catalytic hydrogenation, this process is conveniently carried out by hydrogenation over a noble metal catalyst (for example palladium or carbon) in a suitable solvent until reduction is complete. The resulting compound of formula XXVIII can be isolated by conventional techniques such as recrystallization. When R' is susceptible to hydrogenolysis, the conditions of step (r) may lead directly to a compound of formula XXIX. Otherwise, a selective hydrolysis may be carried out using the conditions described for step (e) in Reaction Scheme I to give a compound of formula XXIX.

The instant invention also comprises all the novel intermediate compounds which are used to prepare the compounds and radicals of the invention.

These novel intermediates are compounds represented by formulas VII, VIII, and IX in Scheme I and formulas XIX, XXI, XXIII, and XXIV in Scheme III and formula XXIX in Scheme IV; wherein the substituents A', B', Z', and R' are as defined in Schemes I-IV except as noted.

The radicals of Formula I may be incorporated into peptides in a protected form, that is $R_1$ or $R_2$ may be substituted alkyl such as tertiary butyl and Z may be hydrogen,

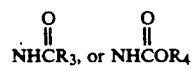

as appropriate. This compound is incorporated into the growing peptide chain according to methods known in the art. The protecting groups are then removed as appropriate according to known methods.

The instant invention also comprises a method for suppressing appetite in subjects by administering to the subject an appetite suppressing effective amount of an analog of CCK wherein the sulfated Tyrosine is substituted with the radical of Formula I.

Particularly preferred is a method for suppressing appetite in subjects by administering to a subject an appetite suppressing effective amount of the following CCK analogs wherein the Sulfated Tyrosine has been substituted with a radical of Formula I:

Most preferred is a method for suppressing appetite in subjects by administering to the subject an appetite suppressing effective amount of the following CCK analogs wherein the sulfated tyrosine has been substituted with a radical of Formula I:

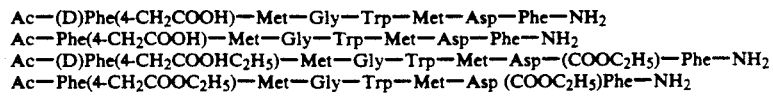

-continued

Ac—Phe(4-tetrazole)—Met—Gly—Trp—Met—Asp—Phe—NH₂

Ac—(D,L)Phe(4-CH₂COOH)—Lys—Gly—Trp—Met—Asp—N—methyl—Phe—NH₂
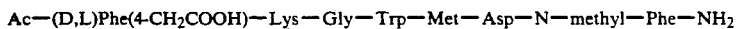

Ac—(D,L)Phe(4-tetrazole)—Lys—Gly—Trp—Met—Asp—N—methyl—Phe—NH₂
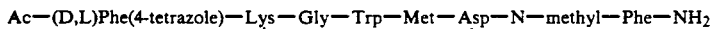

Desamino—Phe(4-tetrazole)Lys—Gly—Trp—Met—Asp—N—methyl—Phe—NH₂
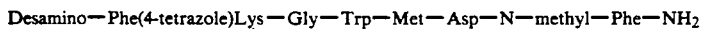

Ac—(D,L)Phe(3-CH₂COOH)—Met—Gly—Trp—Met—Asp—Phe—NH₂
Desamino—Phe(4-CH₂tetrazole)—Met—Gly—Trp—Met—Asp—Phe—NH₂
Desamino—Phe(4
CH₂COOH)—Met—Gly—Trp—Met—Asp—Phe—NH₂
Desamino—Phe(4-tetrazole)—Met—Gly—Trp—Met—Asp—Phe—NH₂

An "appetite suppressing effective amount" as used herein refers to the amount of the peptide (on a weight basis) per kg. of body weight of the subject which must be administered to suppress appetite. It is well within the skill of the art to calculate such amounts considering the method of administration, the particular subject and the weight of the subject. See Morley, J. E. "Minireview. The Ascent of Cholecystokinin (CCK) from Gut to Brain" *Life Sciences*, 30, (1982) 479.

The analogs of the invention may be administered to the subject by any suitable route including, nasal, sublingual, buccal, intraperitoneal, or parenteral including intravenous, intramuscular, or transdermal. The analogs may be administered as water soluble salts, generally as salts of alkaline metals such as sodium or potassium salts, as alkylamine salts, preferably diethylamine salts or as acid addition salts. The analogs of the invention can be converted to the pharmaceutically acceptable salts by known methods.

If the analogs of the invention are administered intranasally such vehicles of administration may include foams, creams, inhalants, etc. The effective appetite suppressing amount of the analog as the active ingredient is dissolved in pharmaceutically acceptable foams or inhalant compositions suitable for intranasal administration, which compositions are known to those skilled in the art.

Where the peptides of the invention are administered parenterally, or intraperitoneally the appropriate amount of the analog as the active ingredient is dissolved in sterile injectable solutions or suspensions. These types of solutions are well known to skilled artisans and comprise for example saline solutions, etc.

PREPARATION OF PEPTIDES OF INVENTION

The peptides of the invention may be prepared using solid phase synthesis by the method generally described by Merrifield, *J. Am. Chem. Soc.*, 85 (1963), 2149, although other equivalent chemical syntheses known in the art may also be used. Solid-phase synthesis is commenced from the C-terminal end of the peptide by coupling a protected α-amino acid by an amide bond to a suitable resin, e.g., benzhydrylamine (BHA), methylbenzhydrylamine (MBHA) or 4-(oxymethyl)-phenylacetamidomethyl (PAM) or 5-[(2' or 4')-aminomethyl-3',5'-dimethoxyphenoxy]valerate (PAL). BHA, MBHA, PAM and PAL resin supports are commercially available.

All solvents used in the peptide preparations described herein, e.g. methylene chloride (CH₂Cl₂), 2-propanol, dimethylformamide (DMF), and methanol, were Burdick and Jackson "distilled in glass" grade and used without additional distillation. Trifluoroacetic acid (TFA), diisopropylethylamine (DIPEA), piperidine (PIP), dicyclohexylcarbodiimide (DCC), 1-hydroxybenzotriazole (HOBt), and [benzotriazole-1-yl-oxytris(dimethyl) phosphonium hexafluorophosphate] (BOP) were purchased from Chemical Dynamics Corp. and were "sequential" grade purity. 1,2-ethanedithiol (EDT) was purchased from Sigma Chemical Co. and used without further purification. All protected amino acids were of the L-configuration unless otherwise indicated and were obtained from Bachem.

In solid phase synthesis, the reactive side chain groups of the various amino acid moieties are typically protected with suitable protecting groups which will prevent a chemical reaction from occurring at that site until the protecting group is ultimately removed. While specific protecting groups are disclosed in regard to the solid phase synthesis aspect, it should be noted that each amino acid can be protected by any protective groups conventionally used for the respective amino acids in solution phase synthesis. Purity of the protected amino acids was confirmed by thin layer chromatography (TLC), elemental analysis, IR, MS, NMR and optical rotation.

The following instrumentation was utilized. TLC was performed on glass backed precoated silica gel 60 F254 plates purchased from Merck using appropriate solvent systems. Detection of spots was by UV fluorescence quenching (254 nm absorption), iodine staining, or ninhydrin spray for primary and secondary amines.

For amino acid analyses, peptides were hydrolyzed in 6N HCl containing phenol at 115° C. for 24 hours in evacuated REACTI-THERM hydrolysis tubes. Analyses were performed on a Beckman 121M amino acid analyzer.

High pressure liquid chromatography (HPLC) was conducted on an LDC apparatus consisting of a CONSTAMETRIC I pump, a CONSTAMETRIC III pump, a GRADIENT MASTER solvent programmer and mixer, and a SPECTROMONITOR III variable wavelength UV detector. Analytical HPLC chromatography was performed on reversed phase with Waters Micro BONDAPACK C₁₈ columns (0.4×25) cm. Preparative HPLC separations were run on (2.5×50) cm PARTISIL M20 10/50 ODS-3 column, or (2.3×30) cm micro BONDAPACK C₁₈ column; in both cases, a pre-column of Whatman Co:Pell ODS pellicular packing was used. The peptides were assembled in a stepwise manner on a solid support using a VEGA 1000 peptide synthesizer. The 1000 peptide synthesizer was controlled by an Apple IIe microprocessor with manual operations at steps 16 and 20 for the Boc-protocol and 7 and 10 for the Fmoc-protocol.

Boc-Phe was coupled to the BHA resin (25 g) using Boc-Phe (6.0 g, 23 mmol), DCC (4.6 g, 22 mmol) and HOBt (4.5 g, 33 mmol) at 0° C. Loading was determined by amino acid analysis to be 0.31 mmol/g resin. Any unreacted amino groups were capped by treatment with 6 equivalents each of acetic anhydride and pyridine.

Boc-N-methyl-Phe was coupled to the BHA resin (8 g) using Boc-N-methyl-Phe (1.35 g, 5 mmol), DCC (1.1 g, 5 mmol) and HOBt (1 g, 8 mmol) at 0° C. Loading was determined by amino acid analysis to be 0.30 mmol/g. Any unreacted amino groups were capped by treatment with 6 equivalents each of acetic anhydride and pyridine.

Boc-Phe-Pam resin was purchased from Vega Biotechnologies, Tucson, Ariz. The loading was 0.32 mmol/g. The PAL-linker was purchased from Biosearch, San Rafael, Calif. The initial synthesis was started with Boc-amino acid resin and portions of peptide resin were removed at various points for separate analog preparation. The protocol for a typical Boc-synthetic cycle was as follows:

| Step | Reagent | Time |
|---|---|---|
| 1 | 1% EDT/CH$_2$Cl$_2$ | 1 × 30 sec. |
| 2 | 50% TFA/CH$_2$Cl$_2$/w 1% EDT | 1 × 1 min. |
| 3 | Repeat Step 1 | |
| 4 | 50% TFA/CH$_2$Cl$_2$/w 1% EDT | 1 × 15 min. |
| 5 | CH$_2$Cl$_2$ | 1 × 30 sec. |
| 6 | Methanol | 1 × 30 sec. |
| 7-8 | Repeat steps 5 and 6 | |
| 9 | CH$_2$Cl$_2$ | 2 × 30 sec. |
| 10 | 8% DIPEA | 2 × 2 min. |
| 11-15 | Repeat step 5-9 | |
| 16 | 3 equiv. Boc-AA, DCC, HOBt | 1 × 60 min. |
| 17 | 1% DIPEA | 1 × 30 min. |
| 18-19 | Repeat steps 6 and 9 | |
| 20-21 | Repeat steps 16 and 17 if Kaiser test is positive | |
| 22 | Methanol | 1 × 30 sec. |
| 23-24 | Repeat steps 5 and 6 | |
| 25 | CH$_2$Cl$_2$ | 1 × 30 sec. |
| 26 | Methanol | 2 × 30 sec. |
| 27 | CH$_2$Cl$_2$ | 3 × 30 sec. |

The protocol for a typical Fmoc-synthetic cycle was as follows:

| Step | Reagent | Time |
|---|---|---|
| 1 | 20% piperidine/DMF | 1 × 5 min. |
| 2 | 20% piperidine/DMF | 1 × 5 min. |
| 3 | DMF | 2 × 1 min. |
| 4 | CH$_2$Cl$_2$ | 2 × 1 min. |
| 5 | 2-propanol | 2 × 1 min. |
| 6 | CH$_2$Cl$_2$/DMF | 2 × 1 min. |
| 7 | 3 equiv. Fmoc-AA, DCC, HOBt | 1 × 60 min. |
| 8 | CH$_2$Cl$_2$ | 2 × 1 min. |
| 9 | DMF | 2 × 1 min. |
| 10-12 | Repeat steps 7, 8, 9 if Kaiser test is positive | |
| 13 | CH$_2$Cl$_2$ | 2 × 1 min. |
| 14 | DMF | 2 × 1 min. |
| 15 | 2-propanol | 2 × 1 min. |
| 16 | DMF | 2 × 1 min. |

Solvents for all washings and couplings were measured to volumes of 10-20 mL/g resin. Couplings were performed using the DCC/HOBt procedure. Coupling reactions were monitored by the Kaiser ninhydrin test to determine whether coupling was complete at step 19 by the Boc-synthetic protocol or at step 9 by the Fmoc-synthetic protocol as set forth by Kaiser et al., *Analytical Biochemistry* 34, 595-598 (1970).

The fully assembled peptide-resins were dried under high vacuum overnight. For the Boc-synthesis the modified procedures of Tam et al. *Tetrahedron Letter*, 23, 4425-4438 (1982) were used. In brief: The peptide-resin was treated in a Teflon tetrafluoroethylene HF apparatus (Peninsula) with HF, dimethylsulfide and p-cresol (5:13:2) for 1 h at 0° C. After evaporation to a low volume fresh anhydrous HF was distilled into the reaction vessel (18 mL) for second treatment for 1.5 h at 0° C. After thorough evaporation, the dry resin was washed with 3 volumes each of Et$_2$O and EtOAc, then triturated with 4×15 mL of 30% acetic acid and filtered. Lyophilization of the aqueous filtrate yielded the crude peptide.

For the Fmoc-synthesis the procedure of Mitchell et al., *J. Org. Chem.*, 43, 2854-2852 (1978) was used. In brief: The peptide-resin was placed in a pressure bottle, suspended in methanol, saturated with NH$_3$ at −20° C. and sealed. The suspension was stirred at room temperature for 2-3 days. After venting the excess NH$_3$, the PAM-resin was filtered off and washed with methanol. The filtrate was evaporated to dryness to give the crude peptide.

Preparative purification was carried out directly on the crude peptide by HPLC on a (2.3×30) cm micro BONDAPACK C$_{18}$ or (2.5×50) cm Whatman ODS-3 column. The peptides were applied in a minimum volume of 50% AcOH, and eluted with a slow gradient (4 hr) of 5-65%, 0.022% TFA/CH$_3$CN, at a flow rate of 8.0 mL/min. Fractions were collected at 3 minute intervals and cuts were made after inspection by analytical HPLC. Fractions, judged to be greater than 97% pure, were pooled and lyophilized.

Purity of the individual peptides was checked by HPLC and determined to be 99% in all cases. Amino acid analyses of the individual peptides were performed and the expected values were obtained in each case. U.V., N.M.R. and M.S. were also performed on the analogs confirming the chemical integrity of the peptides.

The separation of peptides containing (D,L) amino acids into their optically pure enantiomers was achieved by preparative HPLC on (2.3×30) cm micro BONDAPACK C$_{18}$ column from E.S. Industries using CH$_3$CN/0.01M NH$_4$OAC system.

The chirality of the amino acids were determined by the method of Bayer et al. [H. Frank, W. Woiwode, G. Nicholson and E. Bayer (1981), *Liebig Ann. Chem.* 354-365] using glass capillary gas chromatography (GC$^2$).

The present invention will be further described in connection with the following Examples which are set forth for the purposes of illustration only.

For the preparation of the compounds described in Examples 1-36, melting points were taken on a BUCHI 510 melting point apparatus and are uncorrected. Preparative high pressure liquid chromatography (HPLC) was performed on silica gel PRE-PAK 500 cartridges using a Waters Associates Prep LC 500A. Dry dichloromethane was distilled from P$_2$O$_5$, DMF was dried over Linde 3A molecular sieves and triethylamine was distilled from calcium hydride. Concentration refers to evaporation under aspirator vacuum using a Buchi rotary evaporator.

EXAMPLE 1

Preparation of
(S)-4-[[(trifluoromethyl)sulfonyl]oxy]-alpha-]](1,1-dimethylethoxy)carbonyl]amino]benzenepropanoic acid methyl ester A solution of 19.23 g (0.065 mol) of (S)-4-hydroxy-alpha[[(1,1-dimethylethoxy)carbonyl]amino]benzenepropanoic acid methyl ester and 24.0 g (0.067 mol) of N-phenyl-N-trifluoromethylsulfonyl-1,1,1-trifluoromethane sulfonamide in 175 mL of dry dichloromethane was cooled in an ice bath and 9.7 mL (0.70 mol) of triethylamine was added over three minutes. The resulting mixture was held at 0° C. for 1 hour and allowed to warm to room temperature over 1 hour. The reaction mixture was diluted with 500 mL of ether and washed successively with water (1×100 mL), 1N sodium hydroxide solution (2×100 mL), water (1×100 mL), and saturated sodium chloride solution (1×100 mL). The organic phase was dried over magnesium sulfate and concentrated to an oil which was purified by preparative liquid chromatography using silica gel cartridges on a Waters Prep 500 chromatograph, eluting with 20% ethyl acetate-hexane. The pure fractions were combined and evaporated to give 26.78 g (96%) of (S)-4-[[(trifluoromethyl)sulfonyl]oxy]-alpha-[[(1,1-dimethylethoxy)carbonyl]amino]benzenepropanoic acid methyl ester as a colorless oil which crystallized on standing, mp 48°–49° C.

EXAMPLE 2

Preparation of
(S)-alpha-[[(1,1-dimethylethoxy)carbonyl]-amino]-4-(2-propenyl)benzenepropanoic acid methyl ester Argon was passed through a solution of 7.0 g (0.0164 mol) of (S)-4-[[(trifluoromethyl)sulfonyl]oxy]-alpha-[[(1,1-dimethylethoxy)carbonyl]amino]benzenepropanoic acid methyl ester, 5.7 g (0.0165 mol) of allyltributyl tin, and 1.42 g (0.04 mol) of lithium chloride in 50 mL of dimethylformamide for 10 minutes and 210 mg (0.0003 mol) of bis(triphenylphosphine)palladium dichloride was added. The bath temperature was raised to 90°–95° C. for 40 minutes and the mixture was allowed to cool. The mixture was diluted with ether and washed with water and saturated sodium chloride solution and dried over magnesium sulfate. The residue obtained after filtration and evaporation was purified by preparative liquid chromatography using silica gel cartridges on a Waters Prep 500 chromatograph, eluting with 10% ethyl acetate-hexane to give 4.83 g (92%) of (S)-alpha-[[(1,1-dimethylethoxy)carbonyl]amino]-4-(2-propenyl)benzenepropanoic acid methyl ester, mp 56°–59° C.

EXAMPLE 3

Preparation of
(S)-4-carboxymethyl-alpha-[[(1,1-dimethylethoxy)carbonyl]amino]benzenepropanoic acid methyl ester To a solution of 4.00 g (0.0125 mol) of (S)-alpha-[[(1,1-Dimethylethoxy)carbonyl]amino]-4-(2-propenyl)-benzenepropanoic acid methyl ester in 80 mL of carbon tetrachloride and 80 mL of acetonitrile was added a solution of 8.00 g (0.037 mol) of sodium metaperiodate in 200 mL of water. The two phase mixture was stirred mechanically and 0.2 g (0.0001 mol) of ruthenium trichloride hydrate was added. The resulting dark mixture was stirred at room temperature for 1 hour and was diluted with 500 mL of dichloromethane. The layers were separated and the organic layer was washed with water and was dried over magnesium sulfate. Filtration and evaporation gave 3.84 g of a dark oil. This oil was dissolved in 120 mL of t-butyl alcohol and 40 mL of 2-methyl-2-butene and a solution of 12.6 g of sodium chlorite and 12.6 g of sodium dihydrogen phosphate in 80 mL of water was added. The resulting mixture was stirred mechanically for 2 hours. The mixture was diluted with 500 mL of ether, the layers were separated, the organic phase was washed with 100 mL portions of water, 10% sodium thiosulfate and saturated sodium chloride solution and was dried over magnesium sulfate. The residue obtained after filtration and concentration was chromatographed over 150 g of silica gel, eluting with 40:59:1 ethyl acetate-hexane-acetic acid. The earlier fractions contained 0.631 g of a mixture from which (S)-4-carboxy-alpha-[[(1,1-dimethylethoxy)carbonyl]amino]benzenepropanoic acid methyl ester was obtained by crystallization from ether-hexane, mp 101°–104° C., $[\alpha]_D+4.00$ (ethanol). The later fractions were combined, diluted with toluene and evaporated to remove traces of acetic acid and were evacuated under high vacuum for 72 hours to give 3.078 g of (S)-4-carboxymethyl-alpha-[[(1,1-dimethylethoxy)carbonyl]amino]benzenepropanoic acid methyl ester as a colorless oil, dicyclohexylamine salt, mp 141°–143° C., $[\alpha]_D+7.25$ (ethanol).

EXAMPLE 4

Preparation of
(S)-alpha-[[(1,1-dimethylethoxy)-carbonyl]amino]-4-[2-(1,1-dimethylethoxy)-2-oxoethyl]benzene-propanoic acid methyl ester a. A solution of 2.85 g of (S)-4-carboxymethyl)alpha-[[(1,1-dimethylethoxy)carbonyl]amino]benzenepropanoic acid methyl ester in 12 mL of t-butyl alcohol was treated with 2.06 g of dicyclohexylcarbodiimide followed by 0.13 g of 4-pyrrolidinopyridine. A white precipitate formed after a few minutes and the reaction mixture was allowed to stir for 18 hours. The mixture was filtered, and the solid washed with ether. The ether extracts and the filtrate were combined and washed with 1N hydrochloric acid, water, and saturated sodium bicarbonate solution and were dried over magnesium sulfate. The residue obtained after filtration and evaporation was chromatographed over 150 g of silica gel, eluting with 20% ethyl acetate-hexane to afford 1.613 g of (S)-alpha-[[(1,1-dimethylethoxy)carbonyl]amino]-4-[2-(1,1-dimethylethoxy)-2-oxoethyl]benzenepropanoic acid methyl ester as a colorless oil, $[\alpha]_D+6.07$ (ethanol).

b. A solution of 3.50 g of (S)-4-carboxymethyl)-alpha-[[(1,1-dimethylethoxy)carbonyl]amino]benzenepropanoic acid methyl ester in 40 mL of dry toluene and 10 mL of dimethylformamide di-t-butyl acetal was heated to a bath temperature of 80° C. for 4 hours. After cooling, the mixture was diluted with 100 mL of ether and was washed with water and saturated sodium chloride solution and was dried over magnesium sulfate. The residue obtained after filtration and evaporation was chromatographed over 150 g of silica gel, eluting with 20% ethyl acetate-hexane to give 2.663 g of (S)-alpha-[[(1,1-dimethylethoxy)carbonyl]amino]-4-[2-(1,1-dimethylethoxy)2-oxoethyl]benzenepropanoic acid methyl ester.

EXAMPLE 5

Preparation of
(S)-alpha-[[(1,1-dimethylethoxy)carbonyl]amino]-4-[2-(1,1-dimethylethoxy)-2-oxoethyl]benzenepropanoic acid A solution of 1.471 g of (S)-alpha-[[(1,1-dimethylethoxy)carbonyl]amino]-4-[2-(1,1-dimethylethoxy)-2-oxoethyl]-benzenepropanoic acid methyl ester in 25 mL of methanol and 5 mL of 1N sodium hydroxide solution was stirred at room temperature for 2 hours. The mixture was acidified with a slight excess of hydrochloric acid, was diluted with 100 mL of ether, and was washed with water and saturated sodium chloride solution. The residue obtained after filtration and evaporation was chromatographed over 100 g of silica gel, eluting with 40:59:0.5 ethyl acetate-hexane-acetic acid. The product containing fractions were combined, evaporated, diluted with toluene and evaporated finally under high vacuum to give 1.105 g of (S)-alpha-[[(1,1-dimethylethoxy)carbonyl]amino]-4-[2-(1,1-dimethylethoxy)-2-oxoethyl]benzenepropanoic acid $[\alpha]_D + 21.41$ (ethanol).

EXAMPLE 6

Preparation of
5-(4-methylphenyl)-2-(1,1-dimethylethyl)-2H-tetrazole

A solution of 5-(4-methylphenyl)-2H-tetrazole (W. G. Finnegan, R. A. Henry, R. Lofquist *J. Am. Chem. Soc.* 1958, 80, 3908.) (19.9 g, 0.12 mol), t-butanol (19.5 g, 0.26 mol) and concentrated sulfuric acid (5.84 g, 0.06 mol) in trifluoroacetic acid (122 mL) was stirred at room temperature (3 h) and then diluted with ethyl acetate (250 mL). The mixture was washed sequentially with water (2×50 mL), 10% aqueous sodium hydroxide until washings were basic, water (2×30 mL), and then dried over sodium sulfate ($Na_2SO_4$) and filtered. Following removal of the solvents in vacuo, the resultant oil was purified by HPLC on silica gel eluting with 20:1 mixture of hexanes-ethyl acetate to provide 17.5 g of 5-(4-methylphenyl)-2-(1,1-dimethylethyl)-2H-tetrazole as a clear oil, bp. 120°-122° C. (0.3 mm Hg).

EXAMPLE 7

Preparation of benzyl bromide derivatives

N-Bromosuccinimide (NBS) (35.8 g, 0.20 mol) was added in several portions to a solution of 1,1-dimethylethyl 4-methylbenzoate (prepared by the reaction of the respective acid chloride with t-butanol.) (38.0 g, 0.20 mol) and benzoyl peroxide (0.36 g, 1.5 mmol) in carbon tetrachloride (1200 mL) at vigorous reflux. Another portion of benzoyl peroxide (0.36 g, 1.5 mmol) was added just before the final addition of NBS. After the foaming subsided, the reaction mixture was cooled to room temperature, washed with water (2×60 mL) and dried over magnesium sulfate. Filtration and concentration provided an oil that was purified by HPLC on silica gel eluting with a mixture of hexanes and ethyl acetate to give 1,1-dimethylethyl 4-bromomethylbenzoate (21.4 g) in 40% yield.

Following the above procedure, the analogs listed below were prepared.

a. From 1,1-dimethylethyl 3-methylbenzoate (40.0 g, 0.21 mol) there was obtained 1,1-dimethylethyl 3-bromomethylbenzoate (23.0 g, 0.09 mol) in 41% yield.

b. From 1,1-dimethylethyl 2-(4-methylphenyl)acetate (25.0 g, 0.12 mol) there was obtained 1,1-dimethylethyl 2-(4-bromomethylphenyl)acetate (10.9 g, 0.04 mol) in 32% yield.

c. From 5-(4-methylphenyl)-2-(1,1-dimethylethyl)-2H-tetrazole (18 g, 0.08 mol) there was obtained 5-(4-bromomethylphenyl)-2-(1,1-dimethylethyl)-2H-tetrazole (17.4 g, 0.06 mol), in 71% yield.

d. From 1,1-dimethylethyl 2-(4-methylphenyl)-2,2-difluoroacetate (8.0 g, 0.03 mol) there was obtained 1,1-dimethylethyl 2-(4-bromomethylphenyl)-2,2-difluoroacetate (7.7 g, 0.024 mol) in 73% yield.

EXAMPLE 8

Preparation of 5-[(4-bromophenyl)methyl]-2H-tetrazole

4-Bromophenylacetonitrile (30.0 g, 0.15 mol), sodium azide (10.9 g, 0.17 mol) and ammonium chloride (8.9 g, 0.17 mol) were heated in DMF (300 mL) at 90° C. for 2 days. After concentration, water (200 mL) was added to the residue, the mixture was basified with 1M NaOH (170 mL) and washed with ether (2×100 mL). Acidification of the aqueous layer with 1N HCl and collection of the precipitate by suction filtration produced the crude product. This was purified by recrystallization from ethanol to provide 5-[(4-bromophenyl)methyl]-2H-tetrazole (17.2 g, 0.07 mol) in 44% yield, mp. 173°-175° C.

EXAMPLE 9

Preparation of
5-[(4-bromophenyl)methyl]-2-(1,1-dimethylethyl)-2H-tetrazole

A mixture of 5-[(4-bromophenyl)methyl]-2H-tetrazole (18.5 g, 77 mmol), t-butanol (11.4 g, 150 mmol), trifluoroacetic acid (76 mL, 1.0 mol) and concentrated sulfuric acid (3.8 g, 39 mmol) was stirred for 24 h and then partitioned between ethyl acetate (250 mL) and water (100 mL). The organic layer was washed with water (4×100 mL) and 1M NaOH (2×100 mL) and was dried over sodium sulfate. Filtration and removal of the solvent in vacuo produced a solid that was recrystallized from hexane to give 5-[(4-bromophenyl)methyl]-2-(1,1-dimethylethyl)-2H-tetrazole. (12.3 g, 47 mmol) in 54% yield, mp. 69°-70° C.

EXAMPLE 10

Preparation of
4-[[2-(1,1-dimethylethyl)-2H-tetrazol-5-yl]methyl]benzoic acid

To a deoxygenated mixture of 5-[(4-bromophenyl)methyl]-2-(1,1-dimethylethyl)-2H-tetrazole (12.0 g, 41 mmol), triphenylphosphine (11.0 g, 42 mmol), tributylamine (8.4 g, 45 mmol), t-butanol (70 mL) and water (45 mL) was added bis(triphenylphosphine)palladium dichloride (1.0 g, 13 mmol). This mixture was placed in a glass lined autoclave and maintained under carbon monoxide (200 psi) at 100° C. for 2 days. The reaction mixture was diluted with dichloromethane (500 mL), washed with water (3×100 mL) and dried over magnesium sulfate. Filtration and concentration produced the crude product mixture. This was purified by flash chromatography on silica gel using a 4:1 mixture of hexane and ethyl acetate to remove the less polar impurities and 5% acetic acid in hexane-ethyl acetate to elute 4-[[2-(1,1-dimethylethyl)-2H-tetrazole-5-yl]methyl]benzoic acid (4.2 g, 16 mmol) in 49% yield, mp. 139°-140° C.

EXAMPLE 11

Preparation of
4-[[2-(1,1-dimethylethyl)-2H-tetrazol-5-yl]-methyl]benzyl alcohol Diisobutylaluminum hydride (48 mL of a 0.8M solution in toluene, 38 mmol) was added dropwise to a mixture of 4-[[2-(1,1-dimethylethyl)-2H-tetrazole-5-yl]methyl]benzoic acid (2.5 g, 9.6 mmol) in toluene (250 mL) at 0° C. and the mixture was then warmed to room temperature. After stirring overnight, the reaction was quenched at 0° C. by careful addition of a mixture of water and THF (8 mL, 5:3), 10% NaOH (5 mL) and a final portion of water (15 mL). After the addition of ether (200 mL) and stirring at room temperature for 2 hours, the white precipitate was removed by filtration and the filtrate was concentrated. The residue was purified by HPLC on silica gel eluting with a 7:3 mixture of hexane-ethyl acetate to give 4-[[2-(1,1-dimethylethyl)-2-tetrazo;-5-yl]methyl]benzylalcohol (1.6 g, 6.7 mmol) in 70% yield, mp. 65°-66° C.

EXAMPLE 12

Preparation of
5-[[4-(Bromomethyl)phenyl]methyl]-2-(1,1-dimethylethyl)-2H-tetrazole Triphenylphosphine (6.5 g, 25 mmol) was added to a solution of 4-[[2-(1,1-dimethylethyl)-2H-tetrazol-5yl]methyl]benzenemethanol (3.0 g, 12.4 mmol) and carbon tetrabromide (8.3 g, 25 mmol) in diethyl ether (150 mL). After 3 hours the reaction mixture was concentrated and the residue purified by chromatography on silica gel eluting with a 9:1 mixture of hexane-ethyl acetate to give 5-[[4-(bromomethyl)phenyl]methyl]-2-(1,1-dimethylethyl)-2H-tetrazole (2.4 g, 7.8 mmol) in 63% yield, mp. 73°-74° C.

EXAMPLE 13

Preparation of benzyl phenylalaninate-benzophenone imine derivatives

Tetrabutyl ammonium sulfate (3.0 g, 9 mmol) was added to a biphasic mixture consisting of 10% aqueous sodium hydroxide (75 mL), 2-[(diphenylmethylene)amino]acetic acid benzyl ester (3.05 g, 9.3 mmol) and 1,1-dimethylethyl 4-bromomethylbenzoate (3.0 g, 9 mmol) in dichloromethane (58 mL). After several hours of vigorous stirring at room temperature, the reaction mixture was diluted with ether (300 mL) and the layers were separated. The organic layer was washed with water (3×30 mL), dried (K₂CO₃) and filtered. Concentration provided an oil that was purified by HPLC on silica gel (the columns were pre-treated with 10% triethylamine/hexanes, ethyl acetate and finally hexanes) eluting with a mixture of hexanes-ethyl acetate to give rac.-2-](diphenylmethylene)amino]-3-[4-[(1,1-dimethylethoxy)carbonyl]phenyl]propanoic acid benzyl ester, (1.7 g, 3 mmol) in 36% yield.

Following the above procedure, the analogs listed below were prepared.

a. From 1,1-dimethylethyl 3-bromomethylbenzoate (10.0 g, 37 mmol) there was obtained rac.-2-[(diphenylmethylene)amino]-3-[3-[(1,1-dimethylethoxy)carbonyl]phenyl]propanoic acid benzyl ester, (9.4 g, 18 mmol) in 49% yield.

b. From 1,1-dimethylethyl 4-bromomethylphenylacetate (3.1 g, 11 mmol) there was obtained rac.-2-[(diphenylmethylene)amino]-3-[4-[2-(1,1-dimethylethoxy)-2-oxoethyl]phenyl]propanoic acid benzyl ester, (2.9 g, 5 mmol) in 50% yield.

c. From 5-(4-bromomethylphenyl)-2-(1,1-dimethylethyl)-2H-tetrazole (16.0 g, 54 mmol) there was obtained rac.-2-[(diphenylmethylene)amino]-3-[4-[5-[(2-(1,1-dimethylethyl)-2H-tetrazoyl)]]phenyl]propanoic acid benzyl ester, (10.9 g, 32 mmol) in 59% yield.

d. From 5-(4-bromomethylphenylmethyl)-2-(1,1-dimethylethyl)-2H-tetrazole (2.0 g, 6.5 mmol) there was obtained rac.-2-[(diphenylmethylene)amino]-3-[4-[[5-[2-(1,1-dimethylethyl)-2H-tetrazoyl]]methyl]phenyl]propanoic acid benzyl ester, (1.9 g, 3.3 mmol) in 50% yield.

EXAMPLE 14

Preparation of
rac.-2-[(diphenylmethylene)amino]-3-[4-[1,1-difluoro-[2-(1,1-dimethylethoxy)-2-oxoethyl]phenyl]propanoic acid benzyl ester Lithium diisopropyl amide (8.8 mmol) was generated in 25 ml of THF at 0° C. and chilled to −78° C. A solution of 2-[(diphenylmethylene)amino]acetic acid benzyl ester (2.9 g, 8.8 mmol) in THF (5 mL) was added over 5 minutes followed by the dropwise addition of hexamethylphosphoramide (1.6 g, 8.8 mmol) and the mixture was stirred for 15 min. A solution of 1,1-dimethylethyl 2-(4-bromomethylphenyl)-2,2-difluoroacetate (2.7 g, 8.0 mmol) in 5 ml. THF was added slowly and the reaction mixture was warmed over the course of 2 hours to room temperature. The mixture was partitioned between saturated aqueous NH₄Cl (50 mL) and ether (30 mL). The aqueous layer was extracted with additional ether (2×30 mL), and the combined organic layers were washed with brine (20 mL), and dried (MgSO₄). Filtration and concentration yielded an oil that was purified by flash chromatography on silica gel (pretreated with 10% triethylamine in hexanes) eluting with a 9:1 mixture of hexanes-ethyl acetate. This provided rac.-2-[(diphenylmethylene)amino]-3-[4-[1,1-difluoro-[2-(1,1-dimethylethoxy)-2-oxoethyl]phenyl]propanoic acid benzyl ester (3.2 g, 5.6 mmol), as a colorless oil in 71% yield.

EXAMPLE 15

Preparation of benzyl phenylalaninate p-toluenesulfonic acid salt derivatives

A solution of rac.-2-[(diphenylmethylene)amino]-3-[4-[(1,1-dimethylethoxy)carbonyl]phenyl]propanoic acid benzyl ester (11.5 g, 22 mmol) and p-toluenesulfonic acid monohydrate (4.18 g, 22 mmol) in a 10/1 mixture of acetonitrile and water (640 ml) was stirred for 2 h at room temperature. Concentration provided a crude solid product which was recrystallized from ethanol-ether to give rac.-2-amino-3-[4-[(1,1-dimethylethoxy)carbonyl]phenyl]propanoic acid benzyl ester p-toluenesulfonic acid salt, (8.1 g, 15 mmol) in 67% yield, mp. 154°-157° C.

Following the previous procedure, the analogs listed below were prepared.

a. From rac.-2-[(diphenylmethylene)amino]-3-[3-[(1,1-dimethylethoxy)carbonyl]phenyl]propanoic acid benzyl ester (9.4 g, 18 mmol) there was obtained rac.-2-amino-3-[3-[(1,1-dimethylethoxy)carbonyl]phenyl]propanoic acid benzyl ester p-toluenesulfonic acid salt which was carried on to the next step without purification.

b. From rac.-2-[(diphenylmethylene)amino]-3-[4-[2-(1,1-dimethylethoxy)-2-oxoethyl]phenyl]propanoic acid benzyl ester (6.9 g, 13 mmol) there was obtained rac.-2-amino-3-[4-[2-(1,1-dimethylethoxy)-2-oxoethyl]-phenyl]propanoic acid benzyl ester p-toluenesulfonic acid salt, (6.1 g, 11 mmol) in 87% yield, mp. 139°–141° C.

From rac.-2-[(diphenylmethylene)amino]-3-[4-[5-[2-(1,1-dimethylethyl)-2H-tetrazoyl]phenyl]propanoic acid benzyl ester (8.0 g, 15 mmol) there was obtained rac.-2-amino-3-[4-[5-[2-(1,1-dimethylethyl)-2H-tetrazoyl]]phenyl]-propanoic acid benzyl ester p-toluenesulfonic acid salt, (6.6 g, 12 mmol) in 81% yield, mp. 204°–205° C.

d. From rac.-2-[(diphenylmethylene)amino]-3-[4-[1,1-difluoro-[2-(1,1-dimethylethoxy)-2-oxoethyl]phenyl]-propanoic acid benzyl ester (3.2 g, 5.6 mmol) there was obtained raC.-2-amino-3-[4-[1,1-difluoro[2-(1,1-dimethylethoxy)-2-oxoethyl]phenyl]propanoic acid benzyl ester p-toluenesulfonic acid salt, (2.3 g, 3.9 mmol) in 70% yield, mp. 145°–149° C.

e. From rac.-2-[(diphenylmethylene)amino]-3-[4-]]5-[2-(1,1-dimethylethyl)-2H-tetrazoyl]methyl]phenyl]-propanoic acid benzyl ester (4.4 g, 7.9 mmol) there was obtained rac.-2-amino-3-[4-[[5-[2-(1,1-dimethylethyl)-2H-tetrazoyl)]methyl]phenyl]propanoic acid benzyl ester p-toluenesulfonic acid salt, (3.0 g, 5.3 mmol) in 67% yield, mp. 151°–154° C.

EXAMPLE 16

Preparation of rac.-benzyl N-acetylphenylalaninate derivatives

Acetic anhydride (1.0 mL, 10.8 mmol) and triethylamine (2.4 g, 24 mmol) were added sequentially to a solution of rac.-2-amino-3-[4-[(1,1-dimethylethoxy)carbonyl]phenyl]propanoic acid benzyl ester p-toluenesulfonic acid salt (5.0 g, 9 mmol) in dichloromethane (100 ml) at 0° C. After 2 h, the reaction mixture was diluted with dichloromethane (250 mL) and washed with 1N HCl (2×20 mL), saturated aqueous sodium bicarbonate (2×20 mL) and dried (Na$_2$SO$_4$). Filtration and concentration provided the crude product which was purified by HPLC on silica gel eluting with a mixture of hexanes and ethyl acetate to give rac.-2-acetamido-3-[4-[(1,1-dimethylethoxy)carbonyl]phenyl]-propanoic acid benzyl ester (3.3 g, 8 mmol) in 91% yield.

Following the above procedure, the analogs listed below were prepared.

a. From rac.-2-amino-3-[3-[(1,1-dimethylethoxy)-carbonyl]phenyl]propanoic acid benzyl ester p-toluenesulfonic acid salt obtained as the crude product in the hydrolysis of the corresponding diphenylmethyl imine, there was obtained rac.-2-acetamido-3-[3-[(1,1-dimethylethoxy)carbonyl]phenyl]propanoic acid benzyl ester as an oil.

b. From rac.-2-amino-3-[4-[2-(1,1-dimethylethoxy)-2-oxoethyl]phenyl]propanoic acid benzyl ester p-toluenesulfonic acid salt (5.9 g, 11 mmol) there was obtained rac.-2-acetamido-3-[4-[2-(1,1-dimethylethoxy)-2-oxoethyl]]phenyl]propanoic acid benzyl ester, (3.1 g, 8.4 mmol) in 76% yield.

c. From rac.-2-amino-3-[4-[5-[2-(1,1-dimethylethyl)-2H-tetrazoyl]]phenyl]propanoic acid benzyl ester p-toluenesulfonic acid salt (2.0 g, 3.8 mmol) there was obtained rac.-2-acetamido-3-[4-[5-[2-(1,1-dimethylethyl)-2H-tetrazoyl]phenyl]propanoic acid benzyl ester, (1.4 g, 3.3 mmol) in 87% yield.

d. From rac.-2-amino-3-[4-[1,1-difluoro-[2-(1,1-dimethylethoxy)-2-oxoethyl]]phenyl]propanoic acid benzyl ester p-toluenesulfonic acid salt (2.0 g, 3.4 mmol) there was obtained rac.-2-acetamido-3-[4-[1,1-difluoro-[2-(1,1-dimethylethoxy)-2-oxoethyl]]phenyl]propanoic acid benzyl ester, (1.2 g, 2.7 mmol) in 80% yield, mp. 98°–100° C. (ethyl acetate/hexanes).

e. From rac.-2-amino-3-[4-[[5-[2-(1,1-dimethylethyl)-H-tetrazoyl]]methyl]phenyl]propanoic acid benzyl ester p-toluenesulfonic acid salt (4.3 g, 7.4 mmol) there was obtained rac.-2-amino-3-[4-[[5-[2-(1,1-dimethylethyl)-2H-tetrazoyl]]methyl]phenyl]propanoic acid benzyl ester, (2.0 g, 4.6 mmol) in 63% yield, mp. 1143°–114.5° C. (ethyl acetate/hexanes).

EXAMPLE 17

Preparation of N-acetylphenylalanine derivatives

A suspension of rac.-2-acetamido-3-[4-[(1,1-dimethylethoxy)carbonyl]phenyl]propanoic acid benzyl ester (3.3 g, 8 mmol) and 10% Pd/C (320 mg) in ethanol (100 mL) was blanketed with hydrogen (1 atm) at room temperature. Upon the consumption of 1 equivalent of hydrogen, the mixture was filtered through celite. The celite pad was washed with ethanol (50 mL) and the filtrates were combined and concentrated. The resultant solid was purified by recrystallization from ethyl acetate/hexane to give rac.-2-acetamido-3-[4-[(1,1-dimethylethoxy)carbonyl]phenyl]propanoic acid, (2.3 g, 7.4 mmol) in 89% yield, mp. 187°–188° C.

Following the above procedure, the analogs listed below were prepared.

a. From rac.-2-acetamido-3-[3-[(1,1-dimethylethoxy)-carbonyl]phenyl]propanoic acid benzyl ester (3.1 g, 7.8 mmol) there was obtained rac.-2-acetamido-3-[3-[(1,1-dimethylethoxy)carbonyl]phenyl]propanoic acid, (1.8 g, 5.8 mmol) in 75% yield, mp. 164°–166° C. (ethyl acetate/hexanes). b. From rac.-2-acetamido-3-[4-[-2-(1,1-dimethylethoxy)-2-oxoethyl]phenyl]propanoic acid benzyl ester (2.6 g, 6.5 mmol) there was obtained rac.-2-acetamido-3-[4-[2-(1,1-dimethylethoxy)-2-oxoethyl]phenyl]propanoic acid, (1.9 g, 5.9 mmol) in 91% yield, mp. 170°–172° C. (ethyl acetate/hexanes).

c. From rac.-2-acetamido-3-[4-[5-[2-(1,1-dimethylethyl)-2H-tetrazoyl]]phenyl]propanoic acid benzyl ester (3.2 g, 7.6 mmol) there was obtained rac.-2-acetamido-3-[-[5-[(2-(1,1-dimethylethyl)-2H-tetrazoyl]]phenyl]-propanoic acid, (2.2 g, 6.5 mmol) in 86% yield, mp. 206°–207° C. (ethyl acetate/hexanes).

d. From rac.-2-acetamido-3-[4-[1,1-difluoro-[2-(1,1-dimethylethoxy)-2-oxoethyl]phenyl]propanoic acid benzyl ester (1.1 g, 2.5 mmol) there was obtained rac.-2-acetamido-3-[4-[1,1-difluoro[2-(1,1-dimethylethoxy)-2-oxoethyl]phenyl]propanoic acid, (0.6 g, 1.7 mmol) in 69% yield, mp. 149°–150.5° C. (acetonitrile).

e. From rac.-2-acetamido-3-[4-[[5-[2-(1,1-dimethylethyl)-2H-tetrazoyl]]methyl]phenyl]propanoic acid benzyl ester (2.0 g, 4.6 mmol) there was obtained rac.-2-acetamido-3-[4-[[5-[2-(1,1-dimethylethyl)-2H-tetrazoyl]]methyl]phenyl]propanoic acid, (1.2 g, 3.5 mmol) in 76% yield, mp. 193°–194.5° C. (acetonitrile).

EXAMPLE 18

Preparation of
(S)-2-[[(1,1-dimethylethoxy)carbonyl]amino]-3-[4-[[(trifluoromethyl)sulfonyl]oxy]phenyl]propanoic acid
diphenylmethyl ester Triethylamine (4.0 g, 39 mmol) was added dropwise to a suspension of (S)-2-[[(1,1-dimethylethoxy)carbonyl]amino]-3-(4-hydroxyphenyl)propanoic acid diphenylmethyl ester (17.0 g, 38 mmol) and N-phenyl-N-trifluorosulfonyl-1,1,1-trifluoromethyl sulfonamide (13.6 g, 38 mmol) in dichloromethane (170 mL) at 0° C. After 1 hour the reaction mixture was warmed to room temperature and washed with 1N sodium hydroxide (2×25 mL), saturated aqueous sodium bicarbonate (2×25 mL) and water (2×25 mL). The organic layer was dried ($K_2CO_3$), filtered and concentrated. Recrystallization of the solid from hexane gave (S)-2-[[(1,1-dimethylethoxy)carbonyl]amino]-3-[4-[[(trifluoromethyl)sulfonyl]oxy]phenyl]propanoic acid diphenylmethyl ester (13.7 g, 24 mmol) in 62% yield, mp. 110°–112° $[\alpha]_D$—14.23° (0.12% in ethanol).

EXAMPLE 19

Preparation of
(S)-2-[[(1,1-dimethylethoxy)carbonyl]amino]-3-[4-[3-(1,1-dimethylethoxy)3-oxo-1-propenyl]phenyl]-propanoic acid diphenylmethyl ester Bis(triphenylphosphine) palladium dichloride (120 mg, 0.2 mmol) was added to a deoxygenated mixture of (S)-2-[[(1,1-dimethylethoxy)carbonyl]amino]-3-[4-[[(trifluoromethyl)sulfonyl]oxy]phenyl]propanoic acid diphenylmethyl ester (3.0 g, 5.2 mmol), t-butyl acrylate (1.5 mL, 10.2 mmol) and triethylamine (4.0 mL, 30.0 mmol) in DMF (50 mL) and the well-stirred suspension was then heated at 90° C. (24 h). The solvent was removed in vacuo and the resulting residue was purified by flash chromatography on silica gel eluting with a mixture of dichloromethane and hexanes (8:1) to give the (S)-2-[[(1,1-dimethylethoxy)carbonyl]amino]-3-[4-[3-(1,1-dimethylethoxy)-3-oxo-1-propenyl]phenyl]-propanoic acid diphenylmethyl ester (1.6 g, 2.8 mmol) in 54% yield, mp. 135°–137° C., $[\alpha]_D$—5.35° (0.97 % in ethanol).

EXAMPLE 20

Preparation of
(S)-2-[[(1,1-dimethylethoxy)carbonyl]amino]-3-[4-[3-(1,1-dimethylethoxy)-3-oxypropyl]phenyl]propanoic acid (S)-2-[[(1,1-Dimethylethoxy)carbonyl]amino]-3-[4-[3-(1,1-dimethylethoxy)-3-oxo-1-propenyl]phenyl]-propanoic acid diphenylmethyl ester (1.6 g, 2.8 mmol) and 10% Pd/C (300 mg) in t-butanol (20 mL) was blanketed with hydrogen (1 atm). To prevent the solvent from freezing, a warm water bath (40° C.) was used to heat the reaction mixture. Upon the consumption of 2 equivalents of hydrogen, the mixture was filtered through celite. The celite pad was washed with ethanol (50 mL) and the filtrates combined and concentrated. The residue was purified by recrystallization from hexanes to give (S)-2-[[(1,1-dimethylethoxy)carbonyl]amino]-3-[4-[3-(1,1-dimethylethoxy)3-oxopropyl]-phenyl]propanoic acid (1.0 g, 2.6 mmol) in 94% yield, mp. 88.5°–90° C., $[\alpha]_D$—21.2° (0.90% in ethanol).

EXAMPLE 21

Preparation of benzyl 2-(4-bromophenyl)acetate

A mixture of 2-(4-bromophenyl)acetic acid (50 g, 0.23 mol), benzyl alcohol (26 mL, 0.25 mol) and p-toluenesulfonic acid (0.3 g) in 200 ml toluene were heated at reflux with the azeotropic removal of water (15 h). The yellow solution was washed with water (250 mL), saturated aqueous sodium bicarbonate (250 mL) and then dried ($MgSO_4$). Concentration provided a light yellow solid that was recrystallized from cold hexanes to give benzyl 2-(4-bromophenyl)acetate (48.5 g, 0.16 mol) in 69% yield, mp. 47.5°–48° C.

EXAMPLE 22

Preparation of benzyl
(E)-2-[4-[3-(1,1-dimethylethoxy)-3-oxo-1-propenyl]phenyl]acetate A solution of benzyl 2-(4-bromophenyl)acetate (33.5 g, 0.11 mol), t-butyl acrylate (31.6 mL, 0.22 mol) and triethylamine (85 mL, 0.64 mol) in DMF (1000 mL) was deoxygenated with argon, whereupon bis(triphenylphosphine)palladium dichloride (5.1 g, 8.3 mmol) was added. After heating at 75° C. for 12 hours the solvent was removed in vacuo providing a brown residue that was purified by chromatography on silica gel using a mixture of hexanes and ethyl acetate (9:1) to give benzyl (E)-2-[4-[3-(1,1-dimethylethoxy)-3-oxo-1-propenyl]phenyl]acetate as a pale yellow oil (23.3 g, 0.07 mol) in 60% yield.

EXAMPLE 23

Preparation of 1,1-dimethylethyl
4-(carboxymethyl)phenylpropanoate

A mixture of benzyl (E)-2-[4-[3-(1,1-dimethylethoxy)-3-oxo-1-propenyl]phenyl]acetate (11.6 g, 33.0 mmol) and 10% Pd/C (0.5 g) in ethanol (120 mL) was stirred under $H_2$ for 3 hours at 1 atm. Filtration of the mixture through a pad of Celite, followed by concentration gave a colorless oil that was recrystallized from a mixture of ethyl acetate and hexanes to give 1,1-dimethylethyl-4-(carboxymethyl)phenyl propanoate (7.5 g, 28.4 mmol) in 86% yield, mp. 55.5°–56.5° C.

EXAMPLE 24

Preparation of 1,1-dimethylethyl
3-[4-(2-benzyloxy-2-oxo-ethyl)phenyl]propanoate To a stirred suspension of 1,1-dimethylethyl 4-(carboxymethyl)phenylpropanoate (5.3 g, 20.0 mmol) and potassium carbonate (2.8 g, 20.0 mmol) in DMF (30 mL) was added benzyl bromide (3.42 g, 20 mmol). After stirring for 24 h, the solvent was removed in vacuo and the residue was extracted with hexanes (100 mL). Filtration and removal of the solvent under reduced pressure gave 1,1-dimethylethyl 3-[4-(2-benzyloxy-2-oxoethyl)phenyl]propanoate (6.5 g, 18.4 mmol) as a colorless liquid in 92% yield.

EXAMPLE 25

Preparation of
3-[4-(2-benzyloxy-2-oxoethyl)phenyl]propanoic acid 1,1-dimethylethyl 3-[4-(2-benzyloxy-2-oxoethyl)-phenyl]propanoate (3.0 g, 8.5 mmol) was stirred in formic acid (10 mL) for 8 hours. Removal of the solvent in vacuo provided a colorless oil that was shaken vigorously with a mixture of ethyl acetate and hexanes (1:3, 20 mL) until it solidified. The mixture was cooled in ice water and the product, collected by suction filtration to give 3-[4-(2-benzyloxy-2-oxoethyl)phenyl]propanoic acid, as a white solid (2.2 g, 7.4 mmol) in 87% yield, mp. 62°–64.5° C.

EXAMPLE 26

Preparation of N-Hydroxysuccinyl 3-(4-carboxymethyl)phenyl]propanoate

3-[4-(2-benzyloxy-2-oxoethyl)phenyl]propanoic acid (1.10 g; 3.68 mmol) N-Hydroxy succinimide (0.51 g; 4.43 mmol); and 3.86 mL of 1M dicyclohexylcarbodimide in $CH_2Cl_2$ were dissolved in $CH_2Cl_2$ (50 mL). The mixture was stirred at room temperature for 22 hours. Acetic acid 1.0 mL was added and the mixture stirred for 3 hours after which the dicyclohexylurea was removed by filtration. The solvent was removed in vacuo and the residue was redissolved in DMF (40 mL.). After standing approx. 30 min. additional dicyclohexylurea was removed by filtration. The volume was adjusted to 100 mL with additional DMF and the solution was transferred to a pressure bottle. After flushing with $N_2$, 10% Pd/C (1.0 g) was added and the bottle was placed on a Parr hydrogenation apparatus. After flushing the system 3 times with 20 psi; $H_2$ the mixture was shaken under 50 psi $H_2$ for approx. 1½ hour (or until $H_2$ up take ceased.) The pressure bottle was then flushed 3×20 psi $N_2$ before removing from the parr apparatus. The catalyst was removed by filtration through celite and $MgSO_4$. The final volume was adjusted to 140 mL with DMF. 35 mL (0.92 mmol) of the solution of N-hydroxysuccinyl 3-(4-carboxymethyl)phenylpropanoate was used per coupling.

EXAMPLE 27

Preparation of rac.-2-amino-3-hydroxyphenyl)propanoic acid benzyl ester

A 500 mL round bottom flask fitted with a Dean-Stark water separator was charged with a suspension of 10.0 g (0.055 mol) of rac.-3-Hydroxyphenylalanine and 11.5 g (0.066 mol) of p-toluenesulfonic acid monohydrate in 60 mL of benzyl alcohol and 250 mL of toluene. The resulting mixture was heated to reflux for 4 hours as about 2 mL of water was collected in the trap. The mixture was allowed to cool, was diluted with ether and was extracted repeatedly with 1N hydrochloric acid. The combined extracts were neutralized with excess solid sodium bicarbonate to precipitate 8.72 g of rac.-2-amino-3-(3-hydroxyphenyl)propanoic acid benzyl ester.

EXAMPLE 28

Preparation of rac.-2-acetamido-3-hydroxyphenyl)propanoic acid benzy ester

A suspension of 8.72 g (0.032 mol) of rac.-2-amino-3-(3-hydroxyphenyl)propanoic acid benzyl ester in 400 mL of ice cold dichloromethane was treated dropwise with 1.9 mL (0.020 mol) of acetic anhydride. Upon completion of the addition, a solution of 3.70 g of sodium carbonate in 30 mL of water was added simultaneously with an additional 1.9 mL of acetic anhydride. After 1 hour, the layers were separated and the organic layer was washed with water. The combined aqueous layers were extracted with dichloromethane and the combined extracts were washed with brine and dried over magnesium sulfate. Filtration and concentration afforded a residue which was chromatographed on a Waters Prep 500 liquid chromatograph fitted with two silica gel cartridges, eluting with 20% ethyl acetate-hexane to give 8.49 g (84%) of rac.-2-acetamido-3-hydroxyphenyl)propanoic acid benzyl ester as a thick oil.

EXAMPLE 29

Preparation of rac.-2-acetamido-3-[3-[(trifluoromethylsulfonyl)oxy]-phenyl]propanoic acid benzyl ester A solution of 8.30 g (0.026 mol) of rac.-2-acetamido-3-[3-hydroxyphenyl)propanoic acid benzyl ester and 10.0 g (0.028 mol) of N-phenyl-N-trifluoromethyl 1,1,1-trifluoromethyl sulfonyl sulfonamide in 110 mL of freshly distilled dichloromethane was cooled in an ice bath and 4.10 mL (0.029 mol) of triethylamine was added dropwise. The resulting mixture was stirred 1 hour at 0° C. and was allowed to warm to room temperature over 2 hours. The mixture was diluted with 250 mL of ethyl acetate and was washed with successive 50 mL portions of water, 1N sodium hydroxide, 1N hydrochloric acid, water, and brine and was dried over magnesium sulfate. Filtration and concentration afforded an oil which was purified by preparative chromatography on a Waters Prep 500 liquid chromatograph fitted with two Prep-Pak silica gel cartridges, eluting with 40% ethyl acetate-hexane to give 10.02 g (85%) of rac.-2-acetamido-3-[3-[(trifluoromethylsulfonyl)oxy]phenyl]-propanoic acid benzyl ester.

EXAMPLE 30

Preparation of rac.-2-acetamido-3-[3-(2-propenyl)phenyl]propanoic acid benzyl ester Argon was passed through a solution of 9.89 g (0.022 mol) of rac.-2-acetamido-3-[3-(3-trifluoromethylsulfonyl)oxy]phenyl]propanoic acid benzyl ester, 2.8 g (0.066 mol) of lithium chloride, and 7.00 mL (0.0225 mol) of allyltributyltin in 50 mL of dimethylformamide for ten minutes and 0.20 g (0.00028 mol) of bis(triphenylphosphine)palladium dichloride was added. The bath temperature was raised to 95°–100° C. for 2 hours at which time a black precipitate was observed to form. The mixture was cooled, diluted with 250 mL of ether, was washed with 3×50 mL of water and 1×50 mL of brine and was dried over magnesium sulfate. Filtration and concentration afforded an oil which was purified by preparative chromatography on a Waters Prep 500 liquid chromatograph fitted with two silica gel cartridges and eluting with 33% ethyl acetate-hexane to give 6.70 g (85%) of rac.-2-acetamido-3-[3-(2-propenyl)phenyl]propanoic acid benzyl ester as a white solid, mp 55°–56.5° C. A portion was recrystallized from ether-hexane to give mp 57°–58° C.

EXAMPLE 31

Preparation of rac.-2-acetamido-3-[3-(carboxymethyl)phenyl]-propanoic acid benzyl ester Solutions of 6.25 g (0.0185 mol) of rac.-2-acetamido-3-[3-(2-propenyl)phenyl]propanoic acid benzyl ester in 120 mL each of acetonitrile and carbon tetrachloride and 11.9 g (0.0555 mol) of sodium metaperiodate in 240 mL of water were combined and stirred mechanically as 0.25 g (0.0013 mol) of ruthenium chloride hydrate was added to the mixture. The mixture darkened immediately and after 1 hour, was diluted with 300 mL of dichloromethane. The layers were separated and the organic layer was washed with 100 mL of water. The combined aqueous layers were extracted with 200 mL of ether and the combined extracts were dried over magnesium sulfate, filtered and concentrated.

The residue was dissolved in 180 mL of tert-butyl alcohol and 60 mL of 2-methyl-2-butene and a solution of 19.0 g (0.21 mol) of sodium chlorite and 19.0 g (0.137 mol) of monobasic sodium phosphate in 130 mL of water was added all at once. The mixture was stirred at 0° C. for 2 hours, was diluted with ether and the layers were separated. The organic layer was washed with 10% sodium thiosulfate and brine and was dried over magnesium sulfate. Filtration and evaporation gave a oily residue which was chromatographed over 200 g of silica gel eluting with 60:40:1 ethyl acetate-hexane-acetic acid to give 4.64 g of a white solid, mp 129°–139° C. Recrystallization from dichloromethanehexane gave 4.14 g (63%) of rac.-2-acetamido-3-[3-(carboxymethyl)-phenyl]propanoic acid benzyl ester, mp 130°–131° C.

EXAMPLE 32

Preparation of rac.-2-acetamido-3-[3-[2-(1,1-dimethylethoxy)-2-oxoethyl]benzene]propanoic acid benzyl ester A suspension of 4.00 g (0.0113 mol) of rac.-2-acetamido-3-[3-(carboxymethyl)benzene]propanoic acid benzyl ester in 40 mL of toluene and 15 mL of dimethylformamide di-tert-butyl acetal was heated to a bath temperature of 55° C. After 30 min, a clear solution formed and after 3 hours, the mixture was cooled, diluted with 50 mL of ether and washed with 3×25 mL of water, 1×25 mL of brine and was dried over magnesium sulfate. Filtration and concentration gave a white solid which was recrystallized from ether-hexane to afford 3.90 g (84%) of rac.-2-acetamido-3-[3-[2-(1,1-dimethylethoxy)-2-oxoethyl]benzene]propanoic acid benzyl ester, mp 80°–83° C.

EXAMPLE 33

Preparation of rac.-2-acetamido-3-[3-[2-(1,1-dimethylethoxy)-2-oxoethyl]benzene propanoic acid A suspension of 3.30 g (0.00802 mol) of rac.-2-acetamido-3-[3-[2-(1,1-dimethylethoxy)-2-oxoethyl]-propanoic acid benzyl ester in 50 mL of ethanol was hydrogenated over 200 mg of 10% palladium on carbon for 3 hours at room temperature under 1 atmosphere of hydrogen. Hydrogen uptake amounted to 220 mL at which time the mixture was filtered and concentrated to afford 2.54 g of a white solid, mp 167°–170° C. (dec). Recrystallization from ethanol-hexane afforded 1.77 g (69%) of rac.-2-acetamido-3-[3-[2-(1,1-dimethylethoxy)-2-oxoethyl]benzene propanoic acid mp 169°–172° C. (dec).

EXAMPLE 34

Preparation of 1,1-dimethylethyl 4-[[2-(1,1-dimethylethyl)-2H-tetrazol-5-yl]methyl]benzenepropenoate A mixture of Pd(OAc)$_2$ (90 mg, 0.42 mmol) and 1,1'-bis(diphenylphosphino)ferrocene (300 mg, 0.56 mmol) in DMF (40 mL) was heated at 90° C. for 15 minutes while argon was being passed through the mixture. After cooling the burgundy solution to ambient temperature, 5-[(4-bromophenyl)methyl]-2-(1,1-dimethylethyl)-2H-tetrazole (4.0 g, 14 mmol), t-butyl acrylate (3.1 g, 23 mmol) and triethylamine (2.8 mL, 20 mmol) were added to the mixture. The reaction was heated at 90° C. overnite and then concentrated. After filtering the dark mixture through a short column of silica gel using a mixture of hexanes and ethyl acetate (4:1), the fractions containing product were pooled and concentrated. Final purification was achieved by chromatography on a Waters Prep 500 liquid chromatograph fitted with two silica gel cartridges eluting with a mixture of hexanes and ethyl acetate (9:1) to give pure 1,1-dimethylethyl 4-[[2-(1,1-dimethylethyl)-2H-tetrazol-5-yl]methyl]benzene propenoate (3.9 g, 11.3 mmol) in 81% yield. The analytical sample was recrystallized from ethyl acetate and hexanes, mp. 105°–106° C.

EXAMPLE 35

Preparation of 1,1-dimethylethyl 4-[[2-(1,1-dimethylethyl)-2H-tetrazol-5-yl]methyl]benzene propanoate 1,1-dimethylethyl 4-[[2-(1,1-dimethylethyl)-2H-tetrazol-5-yl]methyl]benzene propanoate (3.4 g, 9.9 mmol) in ethanol (30 mL) containing 10% Pd/C (200 mg) was stirred under a blanket of hydrogen (1 atm). After hydrogen uptake ceased, the mixture was filtered through a pad of Celite followed by additional ethanol (30 mL). The filtrate was concentrated and then purified by chromatography on a Waters Prep 500 liquid chromatograph fitted with two silica gel cartridges eluting with a mixture of hexanes and ethyl acetate (4:1) followed by recrystallization from hexanes to give pure 1,1-dimethylethyl 4-[[2-(1,1-dimethylethyl)-2H-tetrazol-5-yl]methyl]benzenepropanoate (3.0 g, 8.6 mmol) in 87% yield, mp. 54°–55° C.

EXAMPLE 36

Preparation of 4-[[2-(1,1-dimethylethyl)-2H-tetrazol-5-yl]methyl]benzene propanoic acid 1,1-dimethylethyl 4-[[2-(1,1-dimethylethyl)-2H-tetrazol-5-yl]methyl]benzenepropanoate (3.0 g, 8.7 mmol) was dissolved in trifluoroacetic acid (33 mL) and stirred at room temperature under argon for 12 hours. The mixture was concentrated and then dissolved in water (50 ml). After adding enough sat. NaHCO$_3$ to raise the pH to 8, the solution was washed with diethyl ether (2×25 mL). The aqueous layer was acidified to pH 3 with 1N HCl and the product collected by suction filtration. Recrystallization from hexanes gave 4-[[2-(1,1-dimethylethyl)-2H-tetrazol-5-yl]methyl]benzenepropanoic acid (1.5 g, 5.7 mmol) in 66% yield, mp. 139°–141° C.

EXAMPLE 37

Preparation of 5-(4-bromophenyl)-2H-tetrazole

4-Bromobenzonitrile (20 g, 110 mmol), sodium azide (7.9 g, 121 mmol) and NH$_4$Cl (6.5 g, 121 mmol) in DMF (340 mL) were heated at 90° C. under argon. After 2 days the reaction mixture was concentrated and then diluted with water (300 mL). After adding enough 1M NaOH to render the mixture basic (litmus paper) it was washed with ether (4×25 mL). The aqueous portion was acidified to pH 3 with 1N HCl, the precipitated product was collected by suction filtration and then washed with water. The crude product was recrystallized from ethanol to give crystalline 5-(4-bromophenyl)-2H-tetrazole (19.2 g, 83.6 mmol) in 76% yield, mp. 271°-273° C.

EXAMPLE 38

Preparation of 5-(4-bromophenyl)-2-(1,1-dimethylethyl)-2H-tetrazole 5-(4-Bromophenyl)-2H-tetrazole (19.0 g, 81.9 mmol), t-butanol (12.1 g, 164 mmol), trifluoroacetic acid (80 mL) and concentrated sulfuric acid (4.6 g, 41 mmol) were stirred at ambient temperature for 24 hours. The mixture was concentrated and dissolved in ethyl acetate (200 mL). After washing with water (3×25 mL), 1M NaOH (3×25 mL) and brine (25 mL) the organic layer was dried ($Na_2SO_4$), filtered and concentrated. The oil was purified by chromatography on a Waters Prep 500 liquid chromatograph fitted with two silica gel cartridges eluting with a mixture of hexanes and ethyl acetate (9:1) to provide 5-(4-bromophenyl)-2-(1,1-dimethylethyl)-2H-tetrazole (17.1 g, 58.1 mmol) as a yellow oil in 71% yield.

EXAMPLE 39

Preparation of 1,1-dimethylethyl 4-[2-(1,1-dimethylethyl)-2H-tetrazol-5-yl]benzenepropenoate A solution of 5-(4-bromophenyl)-2-(1,1-dimethylethyl)-2H-tetrazole (3.0 g, 10.2 mmol), t-butyl acrylate (2.9 mL, 20.4 mmol), and triethylamine (7.9 mL, 59 mmol) in DMF (93 mL) was deoxygenated with argon, whereupon bis(triphenylphosphine)palladium dichloride (0.5 g, 0.8 mmol) was added. After heating at 75° C. for 12 hours the mixture was concentrated under reduced pressure and the brown residue was filtered through a short column of silica gel eluting with a mixture of hexanes and ethyl acetate (9:1). The eluent was concentrated and then purified by chromatography on a Waters Prep 500 liquid chromatograph fitted with two silica gel cartridges eluting with a mixture of hexanes and ethyl acetate (9:1). The fractions containing product were pooled, concentrated and the residue was recrystallized from hexanes to give 1,1-dimethylethyl 4-[2-(1,1-dimethylethyl)-2H-tetrazol-5-yl]benzene propenoate (1.6 g, 5.6 mmol) in 55% yield, mp. 118.5°-120° C.

EXAMPLE 40

Preparation of 5-[4-(3-(1,1-dimethylethoxy)-3-oxopropyl)phenyl]-2-(1,1-dimethylethyl)-2H-tetrazole A suspension of 1,1-dimethylethyl 4-[2-(1,1-dimethylethyl)-2H-tetrazol-5-yl]benzene propenoate (1.6 g, 5.6 mmol) and 100 mg of 10% Pd/c in ethanol (17 mL) was stirred under a blanket of hydrogen (1 atm). After hydrogen uptake ceased, the mixture was filtered through a pad of Celite washing with ethanol (30 mL). The filtrate was concentrated to give 5-[4-(3-(1,1-dimethylethoxy)-3-oxopropyl)phenyl]-2-(1,1-dimethylethyl)-2H-tetrazole (1.2 g, 4.4 mmol) in 78% yield.

EXAMPLE 41

Preparation of 4-[2-(1,1-dimethylethyl)-2H-tetrazol-5-yl]benzenepropanoic acid

5-[4-(3-(1,1-dimethylethoxy)-3-oxopropyl)phenyl]-2-(1,1-dimethylethyl)-2H-tetrazole (1.0 g, 3.7 mmol) was dissolved in trifluoroacetic acid (14 mL) and stirred at room temperature under argon for 12 hours. The mixture was concentrated and then dissolved in water (35 ml). After adding enough sat. $NaHCO_3$ to raise the pH to 8, the solution was washed with diethyl ether (2×10 mL). The aqueous layer was acidified to pH 3 with 1N HCl and the product was collected by suction filtration to give 4-[2-(1,1-dimethylethyl)-2H-tetrazole-5-yl]benzenepropanoic acid (0.7 g, 3.1 mmol) in 84% yield, mp. 88°-90° C.

EXAMPLE 42

Preparation of Ac-(D,L)Phe(3-COOH)-Met-Gly-Trp-Met-Asp-Phe-$NH_2$ 6 g of Boc-Phe-PAM resin (substitution 0.36 mmol/g) was suspended and shaken in $TFA/CH_2Cl_2$ (1:1 by volume, 3×50 mL) 10 min. each time at room temperature to remove the Boc-group. The product was isolated by filtration and washed (3×50 mL each) with $CH_2Cl_2$ 8% DIEA in $CH_2Cl_2$ and $CH_2Cl_2$ to give the free base of Phe-PAM-resin. This was subjected to sequential solid phase synthesis using the Fmoc-protocol. All couplings were performed using the DCC/HOBt procedure. At step 7 the Fmoc-amino acid, DCC, and HOBt were added with the corresponding reaction times as follows: Fmoc-Asp(OtBu)-OH (2.46 g, 6 mmol), DCC (1.24 g, 6 mmol) and HOBt (1.2 g, 9 mmol) were dissolved in 50 mL of 1:1 by volume $DMF/CH_2Cl_2$, and allowed to couple for 60 min at room temperature. Fmoc-Met-OH (2.2 g, 6 mmol), DCC (1.24 g, 6 mmol) and HOBt (1.2 g, 9 mmol) were dissolved in 50 mL of 1:1 by volume $DMF/CH_2Cl_2$, and allowed to couple for 60 min at room temperature. Fmoc-Trp-OH (2.6 g, 6 mmol), DCC (1.24 g, 6 mmol) and HOBt (1.2 g, 9 mmol) were dissolved in 50 mL of 1:1 by volume $DMF/CH_2Cl_2$, and allowed to couple for 60 min at room temperature. Fmoc-Gly-OH (1.8 g, 6 mmol), DCC (1.24 g, 6 mmol) and HOBt (1.2 g, 9 mmol) were dissolved in 50 mL of 1:1 by volume $DMF/CH_2Cl_2$, and allowed to couple for 60 min. Fmoc-Met-OH (2.2 g, 6 mmol), DCC (1.24 g, 6 mmol) and HOBt (1.2 g, 9 mmol) were dissolved in 50 mL of 1:1 by volume $DMF/CH_2Cl_2$, and allowed to couple for 60 min at room temperature. At this point the peptide-resin was dried under high vacuum to provide 7.98 g of Fmoc-Met-Gly-Trp-Met-Asp(OtBu)-Phe-PAM resin.

A portion (1.5 g, 0.4 mmol) of Fmoc-Met-Gly-Trp-Met-Asp-(OtBu)-Phe-PAM resin was deprotected with 20% piperidine/DMF (step 1-6) using the Fmoc protocol and coupled to the compound of Example 17(a), rac.-2-acetamido-3-[3-[1,1-dimethyl ethoxy)carbonyl]-phenyl]propanoic acid [Ac-(D,L)Phe(3-COOtBu)] (400 mg, 1.5 mmol), using DCC (310 mg, 1.5 mmol) and HOBt (270 mg, 2 mmol) which were dissolved in 50 mL of $DMF/CH_2Cl_2$ (1:1) by volume and allowed to react for 60 min at room temperature, then washed (step 8-16), and dried to yield Ac-(D,L)Phe(3-COOtBu)-Met-Gly-Trp-Met-Asp(OtBu)-Phe-PAM-resin. This peptidyl-resin was suspended and shaken in 50% $TFA/CH_2Cl_2$ with 1% EDT (2×50 mL) 10 min each time at room temperature to remove the OtBu groups. The peptidyl-PAM resin was then isolated by filtration, washed (3×50 mL each) with $CH_2Cl_2$, DMF and methanol and placed in a pressure bottle, suspended in 100 mL methanol, saturated with $NH_3$ at −20° C. and sealed. The suspension was stirred at room temperature for 3 days. After venting the excess NH3, the PAM-resin was filtered off and washed with methanol. The combined filtrates were evaporated to dryness to give 1.00 g of crude peptide.

100 mg of the crude peptide was purified by preparative HPLC on a (2.3×30) cm micro Bondapack $C_{18}$ column. The peptide was eluted with a linear gradient (4 h) of 5% to 65%, 0.022% TFA/CH3CN at a flow rate of 8 mL/min, detection at 280 nm. The main peak was collected and lyophilized to yield 25 mg (61%) of Ac-(D,L)Phe(3-COOH)-Met-Gly-Trp-Met-Asp-Phe-NH2. This material was homogeneous by HPLC and gave the correct amino acid analysis and MS. Amino acid analysis: Asp, 1.00(1); Gly, 1.00(1), Met, 1.95(2); Phe, 1.01(1); Trp, 0.80(1); (D,L)Phe(3-COOH), n.d. Empirical Formula: $C_{48}H_{59}N_9O_{12}S_2$. M.W. 1018.18.

EXAMPLE 43

Preparation of
Ac-(D,L)Phe(4-COOH)-Met-Gly-Trp-Met-Asp-Phe-NH2

1.76 g (0.47 mmol) of Fmoc-Met-Gly-Trp-Met-Asp(OtBu)-Phe-PAM-resin obtained from Example 42 was deprotected with 20% piperidine/DMF (step 1-6) using the Fmoc protocol and coupled to the compound of Example 17, rac.-2-acetamido-3-[4-[(1,1-dimethylethoxy)carbonyl]phenyl]propanoic acid [Ac-(D,L)Phe(4-COOtBu)] (700 mg, 1.5 mmol) using DCC (310 mg, 1.5 mmol) and HOBt (270 mg, 2 mmol) which were dissolved in 50 mL of DMF/CH2Cl2 (1:1) by volume and allowed to react for 60 min at room temperature, then washed (step 8-16) and dried to yield Ac-(D,L) Phe (4-COOtBu)-Met-Gly-Trp-Met-Asp(OtBu)-Phe-PAM-resin. This peptidyl-resin was suspended and shaken in 50% TFA/CH2Cl2 with 1% EDT (2×50 mL) 10 min each time ar room temperature to remove the OtBu groups. The peptidyl-resin was then isolated by filtration, washed (3×50 mL each ) with CH2Cl2, DMF and methanol and placed in a pressure bottle suspended in 100 mL of methanol, saturated with NH3 at −20° C. and sealed. The suspension was stirred at room temperature for 3 days. After venting the excess NH3, the PAM-resin was filtered off and washed with methanol. The combined filtrates were evaporated to dryness to yield 541 mg of crude peptide.

80 mg of the crude peptide was purified by preparative HPLC on a (2.3×30) cm micro BONDAPACK $C_{18}$ column. The peptide was eluted with a linear gradient (4h) of 5% to 65%, 0.022% TFA/CH3CN at a flow rate fo 8 mL/min, detection at 280 nm. The main peak was collected and lyophilized to yield 23 mg (33%) of Ac-(D,L)Phe(4-COOH)-Met-Gly-Trp-Met-Asp-Phe-NH2. This material was homogeneous by HPLC and gave the correct amino acid analysis and MS. Amino acid analysis: Asp, 1.00(1); Gly, 0.98(1); Met, 2.00(2); Phe, 1.00(1); Trp, 0.76(1); (D,L)Phe(4-COOH), n.d. Empirical Formula: $C_{48}H_{59}N_9O_{12}S_2$. M.W. 1018.18.

EXAMPLE 44

Preparation of
Ac-(D)Phe(4-COOH)-Met-Gly-Trp-Met-Asp-Phe-NH2

4 mg of Ac-(D,L)Phe-(4-COOH)-Met-Gly-Trp-Met-Asp-Phe-NH2 were dissolved in 0.5 mL of 0.2N NH4OH and applied to (1.25×30) cm micro BONDAPACK $C_{18}$ column form E.S. Industries. The column was previously equilibrated with 10% CH3CN/0.01M NH4OAc and eluted with a linear gradient of 10-40% CH3CN in 0.01M NH4OAc for 120 min at 5 mL/min. The 280 nm absorption of the column effluent was monitored. Two peaks were detected eluting at 78 min at 84 min. Fractions containing these peaks were pooled and lyophilized to 1.5 mg of white powder. Analysis by Glass Capillary Gas Chromatography shows that the compound at 78 min retention time contains the (D)Phe(4-COOH) enantiomer. The purity of this compound was also determined by analytical HPLC, amino acid analysis, UV and IR.

EXAMPLE 45

Prepartion of
Ac-Phe(4-COOH)-Met-Gly-Trp-Met-Asp-Phe-NH2

From Example 44, the compound eluting at 84 min retention time was analyzed by Glass Capillary Gas Chromatography and showed to contain the (L)Phe(4-COOH) enantiomer. The purity of this compound was also determined by analytical HPLC, amino acid analysis, UV and IR.

EXAMPLE 46

Preparation of
Ac-(D,L)Phe(4-CH2COOH)-Met-Gly-Trp-Met-Asp-Phe-Nh2

1.00 g (0.27 mmol) of Fmoc-Met-Gly-Trp-Met-Asp(OtBu)-Phe-PAM-resin obtained from Example 42 was deprotected with 20% piperidine/DMF (step 1-6) using the Fmoc protocol and coupled to the compound of Example 17(b,) rac.-2-acetamido-3-[4-[1,1-dimethylethoxy)-2-oxoethyl]carbonyl]phenyl]propanoic acid [Ac-(D,L)Phe(4-CH2COOtBu)] (280 mg, 0.8 mmol) using the DCC (165 mg, 0.8 mmol) and HOBt (200 mg, 1.5 mmol) which were dissolved in 40 mL DMF/CH2Cl2 (1:1) by volume and allowed to react for 60 min at room temperature, then washed (step 8-16) and dried to yield Ac-(D,L)Phe(4-CH2COOtBu)-Met-Gly-Trp-Met-Asp(OtBu)-Phe-PAM-resin. This peptidyl-resin was suspended and shaken in 50% TFA/CH2Cl2 with 1% EDT (2×50 mL) 10 min each time at room temperature to remove the 0tBu groups. The peptidyl-resin was then isolated by filtration, washed (3×50 mL each) with CH2Cl2, DMF and methanol, and placed in a pressure bottle, suspended in 100 mL of methanol, saturated with NH3 at −20° C. and sealed. The suspension was stirred at room temperature for 3 days. After venting the excess NH3, the PAM-resin was filtered off and washed with methanol. The combined filtrates were evaporated to dryness to yield 392 mg of crude peptide. 80 mg of crude peptide was purified by preparative HPLC on a (2.3×30) cm micro BONDAPACK $C_{18}$ column. The peptide was eluted with a linear gradient (4h) of 5% to 65% 0.022% TFA/CH3CN at a flow rate of 8 mL/min, detection at 280 nm. The main peak was collected and lyophilized to yield 13 mg (24%) of Ac-(D,L)Phe(4-CH2COOH)-Met-Gly-Trp-Met-Asp-Phe-NH2. This material was homogeneous by HPLC and gave the correct amino acid analysis and MS. Amino acid analysis: Asp, 1.02(1); Gly, 1.00(1); Met, 1.96(2); Phe, 1.00(1); Trp, 0.75(1); Phe(4-CH2COOH), 1.00(1). Empirical Formula: $C_{49}H_{61}N_9O_{12}S_2$. M.W. 1032.20.

EXAMPLE 47

Preparation of
Ac-(D)Phe(4-CH$_2$COOH)-Met-Gly-Trp-Met-Asp-Phe-NH$_2$ 2 mg of Ac-(D,L)Phe(4-CH$_2$COOH)-Met-Gly-Trp-Met-Asp-Phe-NH$_2$ were dissolved in 0.5 mL of 0.2N NH$_4$OH and applied to (2.3×30) cm micro Bondapack C$_{18}$ column from E.S. Industries. The column was previously equilibrated with 2% CH$_3$CN/0.01M NH$_4$OAc and eluted with a linear gradient of 2–20% CH$_3$CN in 0.01M NH$_4$OAc over 5 min at 8 mL/min, then held at 20% CH$_3$CN for 120 min. The 280 nm absorption of the column effluent was monitored. Two peaks were detected eluting at 40 min and 56 min. Fractions containing these peaks were pooled and lyophilized to 0.8 mg of white powder. Analysis by Glass Capillary Gas Chromatography shows that the compound eluting at 40 min retention time contains the (D)Phe(4-CH$_2$COOH) enantiomer. The purity of this compound was also confirmed by analytical HPLC, amino acid analysis, UV and IR.

EXAMPLE 48

Preparation of
Ac-Phe(4-CH$_2$COOH)-Met-Gly-Trp-Met-Asp-Phe-NH$_2$

From Example 47, the compound eluting at 46 min retention time was analyzed by Glass Capillary Gas Chromatography and showed to contain the (L)Phe(4-CH$_2$COOH) enantiomer. The purity of this compound was also determined by analytical HPLC, amino acid analysis, UV and IR.

EXAMPLE 49

Preparation of
Ac-(D)Phe(4-CH$_2$COOC$_2$H$_5$)-Met-Gly-Trp-Met-Asp(COOC$_2$H$_5$)-Phe-NH$_2$ 15 mg of Ac-(D,L)Phe(4-CH$_2$COOH)-Met-Gly-Trp-Met-Asp-Phe-NH$_2$ (0.015 mmol) were dissolved in 4 mL of 2:1 by volume ethanol/DMF, HOBt (6 mg, 0.04 mmol) was added and the mixture was cooled to 0° C., DCC (9 mg, 0.04 mmol) was then added and the reaction mixture was stirred for 1 hr at 0° C. and allowed to stand at 5° C. for 24 hours and at room temperature for 15 hours. The reaction mixture was then evaporated in vacuo. The residuo was taken off in 1 mL of DMF and applied into a (2.3×30) cm micro Bondapack C$_{18}$ column. The column was previously equilibrated with 5% CH$_3$CN/0.022% TFA and eluted with a linear gradient of 5–65% CH$_3$CN in 0.022% TFA over 240 min at 8 mL/min. The 280 nm absorption of the column effluent was monitored. Two peaks were detected eluting at 168 min and 171 min. Fractions containing these peaks were pooled and lyophilized to yield 4 mg (49%) of white powder. Analysis by MS, NMR and Glass Capillary Gas Chromatography shows that the compound eluting at 168 min retention time is: Ac-(D)Phe(4-CH$_2$COOC$_2$H$_5$)-Met-Gly-Trp-Met-Asp(COOC$_2$H$_5$)-Phe-NH$_2$. Empirical formula: C$_{53}$H$_{69}$N$_9$O$_{12}$S$_2$. M.W. 1088.31.

EXAMPLE 50

Preparation of
Ac-Phe(4-CH$_2$COOC$_2$H$_5$)-Met-Gly-Trp-Met-Asp-(COOC$_2$H$_5$)-Phe-NH$_2$ From Example 49, the compound eluting at 171 min retention time was analyzed by MS, NMR and Glass Capillary Gas Chromatography and showed to be Ac-Phe(4-CH$_2$COOC$_2$H$_5$)-Met-Gly-Trp-Met-Asp(COOC$_2$H$_5$)Phe-NH$_2$.

EXAMPLE 51

Preparation of
Ac-Phe(4-CH$_2$CH$_2$COOH)-Met-Gly-Trp-Met-Asp-Phe-NH$_2$ 1.76 g (0.47 mmol) of Fmoc-Met-Gly-Trp-Met-Asp(OtBu)-Phe-PAM-resin obtained from Example 42 was deprotected with 20% piperidine/DMF (step 1–6) using the Fmoc protocol and coupled to the compound of Example 20 (S)-2-[[(1,1-dimethylethoxy)carbonyl]amino]-3-[4-[3-(1,1-dimethylethoxy) 3-oxo-1-propenyl]phenyl]propanoic acid [Boc-Phe(4-CH$_2$CH$_2$COOtBu)] (550 mg, 1.5 mmol) using DCC (310 mg, 1.5 mmol) and HOBt (270 mg, 2 mmol) which were dissolved in 50 mL of DMF/CH$_2$Cl$_2$(1:1) by volume and allowed to react for 60 min at room temperature then washed (step 8–16) and dried to yield Boc-Phe(4-CH$_2$CH$_2$COOtBu)-Met-Gly-Trp-Met-Asp(OtBu)-Phe-PAM-resin. This peptidyl-resin was suspended and shaken in 50% TFA/CH$_2$Cl$_2$ with 1% EDT (2×50 mL) 10 min each time at room temperature to remove the Boc and OtBu groups. The peptidyl-resin was then isolated by filtration, washed (3×50 mL each) with CH$_2$Cl$_2$, DMF and methanol, and then acetylated using 3 equivalents of acetic acid and BOP reagent in the presence of 1.5% DIEA according to the same protocol as used for the Boc-amino acid residues. The acetylated peptidyl-resin was then placed in a pressure bottle, suspended in 75 mL of methanol saturated with NH$_3$ at −20° C. and sealed. The suspension was stirred at room temperature for 3 days. After venting the excess NH$_3$, the PAM resin was filtered off and washed with methanol and 90% acetic acid. The combined filtrates were evaporated and the residue lyophilized to yield 831 mg of crude peptide. 100 mg crude peptide was purified by preparative HPLC on a (2.3×30) cm micro BONDAPACK C$_{18}$ column. The peptide was eluted with a linear gradient (4h) of 5% to 65% 0.022% TFA/CH$_3$CN at a flow rate of 8 mL/min, detection at 280 nm. The main peak was collected and lyophilized to yield 17 mg (29%) of Ac-Phe(4-CH$_2$CH$_2$COOH)-Met-Gly-Trp-Met-Asp-Phe-NH$_2$. This material was homogeneous by HPLC and gave the correct amino acid analysis and MS. Amino acid analysis: Asp, 1.00(1); Gly, 1.01(1); Met, 1.95(2); Phe, 1.00(1); Phe(CH$_2$CH$_2$COOH), 0.97(1); Trp, 0.70(1). Empirical Formula: C$_{50}$H$_{63}$N$_9$O$_{12}$S$_2$. M.W. 1046.22.

EXAMPLE 52

Preparation of
Ac-(D,L)Phe(4-CF$_2$COOH)-Met-Gly-Trp-Met-Asp-Phe-NH$_2$ 1.00 g (0.27 mmol) of Fmoc-Met-Gly-Trp-Met-Asp(OtBu)-Phe-PAM-resin obtained from Example 42 was deprotected with 20% piperidine/DMF (step 1–6) using the Fmoc protocol and coupled to the compound of Example 17(d), rac. -2-acetamido-3-[4-[1,1-difluoro[2-(1,1-dimethylethoxy)-2-oxoethyl]phenyl]-propanoic acid [Ac-(D,L)Phe(4-CF$_2$COOtBu)] (310 mg, 0.8 mmol) using the DCC (165 mg, 0.8 mmol) and HOBt (200 mg, 1.5 mmol) which were dissolved in 40 mL DMF/CH$_2$Cl$_2$ (1:1) by volume and allowed to react for 60 min at room temperature then washed (step 8–16) and dried to yield Ac-(D,L)Phe(4-CF$_2$COOtBu)-Met-Gly-Trp-Met-Asp(OtBu)-Phe-PAM-resin. This peptidyl-resin was suspended and shaken in 50% TFA/CH$_2$Cl$_2$ with 1% EDT (2×50 mL) 10 min each time at room temperature to remove the OtBu groups. The peptidyl-resin was then isolated by filtration, washed (3×50 mL each) with CH$_2$Cl$_2$, DMF and methanol and placed in a pressure bottle suspended in 100 mL of methanol, saturated with NH$_3$ at −20° C. and sealed. The suspension was stirred at room temperature for 3 days. After venting the excess NH$_3$, the PAM-resin was filtered off and washed with methanol. The combined filtrates were evaporated to dryness to yield 388 mg of crude peptide. 70 mg of the crude peptide was purified by preparative HPLC on a (2.3×30) cm micro BONDAPACK C$_{18}$ column. The peptide was eluted with a linear gradient (4 h) of 5 to 65% 0.022% TFA/CH$_3$CN at a flow rate of 8 mL/min, detection at 280 nm. The main peak was collected and lyophilized to yield 14 mg (27%) of Ac-(D,L)Phe(CF$_2$COOH)-Met-Gly-Trp-Met-Asp-Phe-NH$_2$. This material was homogeneous by HPLC and gave the correct amino acid analysis and MS. Amino acid analysis: Asp, 1.00(1); Gly, 1.00(1); Met, 2.04(2); Phe, 1.00(1); Trp, 0.70(1); Phe(4CF$_2$COOH) n.d. Empirical Formula: C$_{49}$H$_{59}$N$_9$O$_{12}$F$_2$S$_2$. M.W. 1068.20.

EXAMPLE 53

Preparation of Ac-(D,L)Phe(4-tetrazole)-Met-Gly-Trp-Met-Asp-Phe-NH$_2$

Boc-Phe (2.6 g, 10 mmol) and HOBt (2.0 g, 15 mmol) were dissolved in a mixture of 20 mL CH$_2$Cl$_2$ and 20 mL DMF chilled to 0° C. and with stirring (2.06 g, 10 mmol) DCC was added and the mixture was stirred for 60 minutes at 0 C. Separately 10 g of benzhydrylamine copolysterene 1% divinylbenzene cross-linked resin (0.56 mmole N/g) was washed with 10% diisopropylethylamine in methylene chloride for 30 min, filtered and washed with methylene chloride dimethylformamide and methylene chloride. The chilled mixture above was added to the resin and stirred for 24 hours at room temperature. The resin was filtered and washed with methylene chloride, dimethylformamide, isopropanol, methylene chloride, dimethylformamide, isopropanol, methylene chloride and dried under high vacuum. Amino acid analysis showed the resin to contain 0.32 mmoles of phenylalanine per gram of resin. Unreacted amino groups were capped by shaking the resin with 5 mL of acetic anhydride and 5 mL diisopropylethylamine in methylene chloride for 60 minutes. The resin was filtered and washed with methylene chloride, isopropanol, dimethylformamide and methylene chloride. 1.5 g (0.48 mmol) Boc-Phe-BHA resin was subjected to sequential solid phase synthesis using the Boc protocol. All couplings were performed using the DCC/HOBt procedure. At step 16 the Boc-amino acid, DCC and HOBt were added with the corresponding reaction times as follows: Boc-Asp(OBzl)-OH (485 mg, 1.5 mmol), DCC (310 mg, 1.5 mmol) and HOBt (270 mg, 2 mmol) were dissolved in 20 mL of 1:1 by volume DMF/CH$_2$Cl$_2$, and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Trp(For)-OH (500 mg, 1.5 mmol), DCC (310 mg, 1.5 mmol) and HOBt (270 mg, 2 mmol) were dissolved in 20 mL of DMF, and allowed to couple for 60 min at room temperature. Boc-Gly-OH (270 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. The compound of Example 17(c), rac.-2-acetamido-3-[4-[5-(2-(1,1-dimethylethyl)-2H-tetrazoyl]]phenyl]propanoic acid [Ac-(D,L)Phe(4-tetrazole-tBu)] (500 mg, 1.5 mmol), DCC (310 mg, 1.5 mmol) and HOBt (270 mg, 2 mmol) were dissolved in 20 mL of 1:1 by volume DMF/CH$_2$Cl$_2$, and allowed to couple for 60 min at room temperature. At this point the peptidyl-resin was dried under high vacuum to provide 2.25 g of Ac-(D,L)Phe(4-tetrazole-tBu)-Met-Gly-Trp(For)-Met-Asp(OBzl)-Phe-BHA-resin.

2.25 g of the resin was cleaved by treatment with 5 mL of HF containing 2.0 mL of anisole, 1.0 mL of EDT and 15 mL of dimethylsulfide for 1 hour at 0° C. After evaporation to a low volume, fresh anhydrous HF (20 mL) was distilled into the reaction vessel for a second treatment for 2 h at 0° C. After thorough evaporation, the resin was washed with 2 volumes of ethylacetate then triturated with 4×15 mL of 30% acetic acid, filtered and lyophilized to yield 415 mg of crude peptide.

100 mg of the crude peptide was purified by preparative HPLC on a (2.3×30) cm micro BONDAPACK C$_{18}$ column. The peptide was eluted with a linear gradient (4 h) of 5 to 65% 0.022% TFA/CH$_3$CN of a flow rate of 8 mL/min, detection at 280 nm. The main peak was collected and lyophilized to yield 8 mg (6.6%) of Ac-(D,L)Phe(4-tetrazole)-Met-Gly-Trp-Met-Asp-Phe-NH$_2$. This material was homogeneous by HPLC and gave the correct amino acid analysis and MS. Amino acid analysis: Asp, 0.98(1); Gly, 1.00(1); Met, 1.92(2); Phe, 1.00(1); (D,L)Phe(4-tetrazole), 0.96(1); Trp, n.d. Empirical Formula: C$_{48}$H$_{59}$N$_{13}$O$_{10}$S$_2$. M.W. 1042.19.

EXAMPLE 54

Preparation of Ac-(D)Phe(4-tetrazole)-Met-Gly-Trp-Met-Asp-Phe-NH$_2$ 2 mg of Ac-(D,L)Phe(4-tetrazole)-Met-Gly-Trp-Met-Asp-Phe-NH$_2$ were dissolved in 0.5 mL of 0.2N NH$_4$OH and applied to (2.3×30) cm micro Bondapack C$_{18}$ column from E.S. Industries. The column was previously equilibrated with 1% CH$_3$CN/0.01M NH$_4$OAc and eluted with a step gradient of 1–20% CH$_3$CN/0.01M NH$_4$OAc over 5 min at 8 mL/min, then 20–30% CH$_3$CN/0.01M NH$_4$OAc over 120 min at 8 mL/min. The 280 nm absorption of the column effluent was monitored. Two peaks were detected eluting at 35 min and 39 min. Fractions containing these peaks were pooled and lyophilized to 1 mg of white powder. Analysis by Glass Capillary Gas Chromatography shows that the compound eluting at 35 min retention time contains the (D)Phe(4-tetrazole) enantiomer. The purity of this compound was also confirmed by analytical HPLC, amino acid analysis, UV and IR.

EXAMPLE 55

Preparation of
Ac-Phe(4-tetrazole)-Met-Gly-Trp-Met-Asp-Phe-NH$_2$

From Example 54, the compound eluting at 39 min retention time was analyzed by Glass Capillary Gas Chromatography and shown to contain the (L)Phe(4-tetrazole) enantiomer. The purity of this compound was also determined by analytical HPLC, amino acid analysis, UV and IR.

EXAMPLE 56

Preparation of
Ac-(D,L)Phe(4-CH$_2$COOH)-Lys-Gly-Trp-Met-Asp-N-methyl-Phe-NH$_2$ Boc-N-methyl-Phe (5 g, 17.8 mmol) and HOBt (34 g, 25 mmol) were dissolved in a mixture of 20 mL CH$_2$Cl$_2$ and 20 mL DMF chilled to 0° C. and with stirring (4.12 g, 20 mmol) DCC was added and the mixture was stirred for 60 minutes at 0° C. Separately 10 g of benzhydrylamine copolysterene 1% divinylbenzene cross-linked resin (0.39 mmol N/g) was washed with 10% diisopropylethylamine in methylene chloride for 30 min, filtered and washed with methylene chloride dimethylformamide and methylene chloride. The chilled mixture above was added to the resin and stirred for 24 hours at room temperature. The resin was filtered and washed with methylene chloride, dimethylformamide, isopropanol, methylene chloride, and dried under high vacuum. Amino acid analysis showed the resin to contain 0.30 mmoles of N-methylphenylalanine per gram of resin. Unreacted amino groups were capped by shaking the resin with 5 mL of acetic anhydride and 5 mL diisopropylethylamine in methylene chloride for 60 min. The resin was filtered and washed with methylene chloride, isopropanol, dimethylformamide and methylene chloride.

4 g (1.2 mmol) Boc-N-methyl-Phe-BHA resin was suspended and shaken in TFA/CH$_2$Cl$_2$ (1:1) by volume (3×40 mL) 10 min, each time at room temperature to remove the Boc group. The product was isolated by filtration and washed (3×50 mL each) with CH$_2$Cl$_2$, 8% DIEA in CH$_2$Cl$_2$ and CH$_2$Cl$_2$ to give the free base of N-methyl-Phe-BHA resin. This was subjected to sequential solid phase peptide synthesis using the DCC/HOBt procedure. At step 7 the Fmoc amino acid, DCC and HOBt were added with the corresponding reaction times as follows: Fmoc-Asp(OtBu)-OH (1.64 g, 4 mmol), DCC (825 mg, 4 mmol) and HOBt (810 mg, 6 mmol) were dissolved in 40 mL of 1:1 by volume DMF/CH$_2$Cl$_2$, and allowed to couple for 60 min at room temperature. Fmoc-Met-OH(1.5 g, 4 mmol), DCC (825 mg, 4 mmol) and HOBt (810 mg, 6 mmol) were dissolved in 40 mL of 1:1 by volume DMF/CH$_2$Cl$_2$, and allowed to couple for 60 min at room temperature. Fmoc-Gly-OH (1.2 g, 4 mmol), DCC (825 mg, 4 mmol) and HOBt (810 mg, 6 mmol) were dissolved in 40 mL of 1:1 by volume DMF/CH$_2$Cl$_2$, and allowed to couple for 60 min at room temperature. Fmoc-Lys(Boc) as is (1.9 g, 4 mmol), DCC (825 mg, 4 mmol) and HOBt (810 mg, 6 mmol) were dissolved in 40 mL of 1:1 by volume DMF/CH$_2$Cl$_2$, and allowed to couple for 60 min. At this point the peptide-resin was dried under high vacuum to provide 5.2 g of Fmoc-Lys(Boc)-Gly-Trp-Met-Asp(OtBu)-N-methyl-Phe-BHA-resin. This peptidyl-resin was suspended and shaken in 50% TFA/CH$_2$Cl$_2$ with 1% EDT (2×50 mL) 10 min each time at room temperature to remove the OtBu and the Boc groups. The peptidyl-BHA resin was then neutralized with 8% DIPEA in CH$_2$Cl$_2$, washed (3×50 mL each) with CH$_2$Cl$_2$, DMF and methanol, and isolated by filtration to yield Fmoc-Lys-Gly-Trp-Met-Asp-N-methyl-Phe-BHA resin. The cyclization on the resin between the ε-amino group of Lys and the β-carboxyl group of Asp was achieved using the BOP reagent (2.0 g, 4 mmol) in DMF (50 mL) containing 1.5% DIEA (v/v) for 48 h. A negative Kaiser ninhydrin test was observed and the peptide-resin was washed and dried to yield:

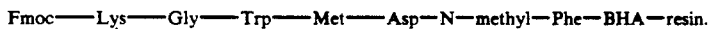

Fmoc—Lys—Gly—Trp—Met—Asp—N—methyl—Phe—BHA—resin.

1.1 g (0.33 mmol) of Fmoc-Lys-Gly-Trp-Met-Asp-N-methyl-Phe-BHA-resin was deprotected with 20% piperidine/DMF (step 1-6) using the Fmoc protocol and coupled to the Compound of Example 17(b), rac.-2-acetamido-3-[4-[(1,1-dimethylethoxy)-2-oxoethyl]-phenyl]propanoic acid [Ac-(D,L)Phe(4-CH$_2$COOtBu)] (350 mg, 1 mmol) using DCC (210 mg, 1 mmol) and HOBt (202 mg, 15 mmol) which were dissolved in 40 mL DMF/CH$_2$Cl$_2$ (1:1) by volume and allowed to react for 60 min at room temperature, then washed (step 8-16) and dried to yield 1.2 g Ac-(D,L)Phe(4-CH$_2$COOtBu)-Lys-Gly-Trp-Met-Asp-N-methyl-Phe-BHA-resin. This peptidyl-resin was suspended and shaken in 50% TFA/CH$_2$Cl$_2$ with 1% EDT (2×20 mL) 10 min each time at room temperature to remove the OtBu group, washed (3×50 mL each) with CH$_2$Cl$_2$ and dried in vacuo. The peptide was cleaved from the resin by treatment with 15 mL of HF containing 1.0 mL of anisole, 0.5 mL of DTE for 2 hours at 0° C. After thorough evaporation, the resin was washed with 2 volumes of ethylacetate, then triturated with 4×15 mL of 30% acetic acid, filtered and lyophilized to yield 200 mg of crude peptide.

100 mg of the crude peptide was purified by preparative HPLC on a (2.3×30) cm micro BONDAPACK C$_{18}$ column. The peptide was eluted with a linear gradient (4 h) of 5 to 65% 0.022% TFA/CH$_3$CN of a flow rate of 8 mL/min, detection at 280 nm. The main peak was collected and lyophilized to yield 12 mg (7%) of:

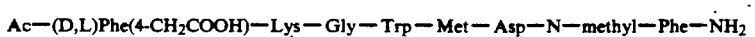

Ac—(D,L)Phe(4-CH$_2$COOH)—Lys—Gly—Trp—Met—Asp—N—methyl—Phe—NH$_2$

DCC (825 mg. (1 mmol) and HOBt (810 mg, 6 mmol) were dissolved in 40 ml of 1:1 by volume DMF/CH$_2$Cl$_2$, and allowed to couple for 60 min. at room temperature. Fmoc-Trp-OH (1.7 g, 4 mmol), This material was homogeneous by HPLC and gave the correct amino acid analysis and MS. Amino acid analysis: Asp, 1.08(1); Gly, 1.00(1); Met, 1.00(1); Lys, 0.95(1); Phe(4-CH$_2$COOH), 0.92(1); N-methyl-Phe (n.d.); Trp, 0.70(1). Empirial Formula: C$_{51}$H$_{64}$N$_{10}$O$_{11}$S$_1$. M.W. 1025.18.

EXAMPLE 57

Preparation of Ac-(D,L)Phe(4-tetrazole)-Lys-Gly-Trp-Met-Asp-N-methyl-Phe-NH$_2$ 1.1 g (0.33 mmol) of Fmoc-Lys-Gly-Trp-Met-Asp-N-methyl-Phe-BHA-resin obtained from Example 56 was deprotected with 20% piperidine/DMF (step 1-6) using the Fmoc protocol and coupled to the Compound of Example 17(c), rac.-2-acetamido-3-[4-[5-2-(1,1-dimethylethyl)-2H-tetrazoyl]]phenyl]propanoic acid [Ac-(D,L)Phe(4-tetrazole-tBu)] (500 mg, 1.5 mmol), using DCC (310 mg, 1.5 mmol), and HOBt (270 mg, 2 mmol) which were dissolved in 40 mL DMF/CH$_2$Cl$_2$ (1:1) by volume and allowed to react for 60 min at room temperature, then washed (step 8-16) and dried to yield 1.2 g of:

Ac-(D,L)Phe(4-tetrazole-tBu)-Lys-Gly-Trp-Met-Asp-N-methyl-Phe-BHA resin which was cleaved by treatment with HF (15 mL) containing 1.0 mL anisole, 0.5 mL DTE, and 0.5 mL dimethylsulfide for 2 h at 0° C. After thorough evaporation, the resin was washed with 2 volumes of ethylacetate, then triturated with 4×15 mL of 30% acetic acid, filtered and lyophilized to yield 123 mg of crude peptide.

123 mg of the crude peptide was purified by preparative HPLC on a (2.3×30) cm micro BONDAPACK C$_{18}$ column. The peptide was eluted with a linear gradient (4 h) of 5 to 65% 0.022% TFA/CH$_3$CN at a flow rate of 8 mL/min, detection at 280 nm. The main peak was collected and lyophilized to yield 20 mg (6%) of:

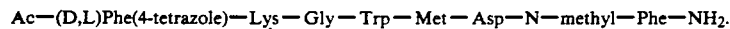

Ac—(D,L)Phe(4-tetrazole)—Lys—Gly—Trp—Met—Asp—N—methyl—Phe—NH$_2$.

This material was homogeneous by HPLC and gave the correct amino acid analysis and MS. Amino acid analysis: Asp, 1.00(1); Gly, 1.00(1); Met, 1.03(1); Lys, 1.01(1); Trp, 0.6(1); Phe(4-tetrazole); 0.97(1); N-methyl-Phe, n.d. Empirical Formula: C$_{50}$H$_{62}$N$_{14}$O$_9$S. M.W. 1035.90.

EXAMPLE 58

Preparation of Ac-(D,L)Phe-(3-CH$_2$COOH)-Met-Gly-Trp-Met-Asp-Phe-NH$_2$ 1.00 g (0.87 mmol) of Fmoc-Met-Gly-Trp-Met-Asp(ot Bu)-Phe-PAM-resin obtained from Example 42 was deprotected with 20% piperidine/DMF (step 1-6) using the Fmoc protocol and coupled to the Compound of Example 33, rac.-N-acetyl-3-[2-(1,1-dimethylethoxy)-2-oxoethyl]phenylalanine [Ac-(D,L)Phe(3-CH$_2$CO$_2$tBu)] (280 mg 0.8 mmol) using DCC (165 mg. 0.8 mmol) and HOBt (200 mg. 1.5 mmol) which were dissolved in 40 ml DMF/CH$_2$Cl$_2$ (1:1) by volume and allowed to react for 60 min at room temperature. Then washed (step 8-16) and dried to yield Ac-(D,L,)Phe(3-CH$_2$COOtBu)-Met-Gly-Trp-Met-Asp(OtBu)-Phe-PAM resin. This piptidyl-resin was suspended and shaken in 50% TFA/CH$_2$Cl$_2$ with 1% EDT (2×50 ml) 10 min each time at room temperature to remove the OtBu groups. The peptidyl-resin was then isolated by filtration, washed (3×50 ml each) with CH$_2$Cl$_2$, DMF and methanol, and placed in a pressure bottle suspended in 100 ml of methanol, saturated with NH$_3$ at 20° and sealed. The suspension was stirred at room temperature for 3 days. Ater venting the excess NH$_3$, the PAM-resin was filtered off and washed with methanol. The combined filtrates were evaporated to dryness to yield 456 mg of crude peptide. 80 mg of the crude peptide was purified by preparative HPLC on a (2.3×30) cm micro BONDAPACK C$_{18}$ column. The peptide was eluted with a linear gradient (4 h) of 5 to 65% 0.022%. TFA/CH$_3$CN of a flow rate at 8 ml/min. detection at 280 nm. The main peak was collected and lyophilized to yield 14 mg (25%) of Ac-(D,L)Phe(3-CH$_2$COOH)-Met-Gly-Trp-Met-Asp-Phe-NH$_2$. This material was homogeneous by HPLC and gave the correct amino acid analysis and MS Amino acid analysis: Asp 1.00 (1); Gly 0.80 (1); Met 2.08 (2); Phe 1.00 (1); Trp 0.70 (1); Phe(3CH$_2$COOH) 1.00 (1); Empirical Formula C$_{49}$H$_{61}$N$_9$O$_{12}$S$_2$ M.W. 1032.20.

EXAMPLE 59

Preparation of Desamino Phe(4-CH$_2$COOH)-Met-Gly-Trp-Met-Asp-Phe-NH$_2$ 1.00 g (0.87 mmol) of Fmoc-Met-Gly-Trp-Met-Asp-(OtBu)-Phe-PAM resin obtained from example 42 was deprotected with 20% piperidine/DMF (Step 1-6) using the Fmoc protocol and coupled to the Compound of Example 26, N-hydroxysuccinyl 3-(4-carboxymethyl)phenylpropaonate, [Des amino Phe(4-CH$_2$COOH)ONSu ester] (244 mg. 0.8 mmol) which was dissolved in 20 ml of DMF/CH$_2$Cl$_2$ (1:1) by volume and allowed to react for 24 hours at room temperature, then washed (step 8-16) and dried to yield Des amino Phe(4-CH$_2$COOH)-Met-Gly-Trp-Met-Asp(OtBu)-Phe-PAM resin. This peptidyl-resin was suspended and shaken in 50% TFA/CH$_2$Cl$_2$ with 1% EDT (2×50 ml) 10 min each time at room temperature to remove the OtBu group. The peptidyl-resin was then isolated by filtration, washed (3×50 ml each) with CH$_2$Cl$_2$, DMF and methanol, and placed in a pressure bottle, suspended in 100 ml of methanol, saturated with NH$_3$ at −20° C. and sealed. The suspension was stirred at room temperature for 3 days. After venting the excess NH$_3$, the PAM-resin was filtered off and washed with methanol. The combined filtrates were evaporated to dryness to yield 733 mg of crude peptide. 80 mg of the crude peptide was purified by preparation. HPLC on a (2.3×30 cm) micro Bondapack C$_{18}$ column. The peptide was eluted with a linear (4 h) of 5 to 65% 0.022%. TFA/CH$_3$CN at a flow rate of 8 ml/min. detection of 280 nm. The main peak was collected and lyophilized to yield 8 mg (38%) of Des amino Phe(4-CH$_2$COOH)-Met-Gly-Trp-Met-Asp-Phe-NH$_2$. This material was homogeneous by HPLC and give the correct amino acid analysis and MS. Amino acid analysis: Asp 1.00 (1); Gly 1.00 (1); Met 2.00(2); Phe 1.00 (1); Trp 0.71 (1); Empirical formula C$_{47}$H$_{58}$N$_8$O$_{11}$S$_2$ MW 975.2.

EXAMPLE 60

Preparation of
Ac-(D,L)Phe(4-CH$_2$tetrazole)-Met-Gly-Trp-Met-Asp-Phe-NH$_2$ 1.5 g (0.48 mmol) Boc-Met-Gly-Trp(For)-Met-Asp(OBZl)phe-BHA resin obtained from example 53 was deprotected with 50% TFA/CH$_2$Cl$_2$ with 1% EDT (step 1-15) using the Boc protocol and coupled to the compound of Example 17(e), rac.-2-amino-3-[4-[[5-[2-(1,1-dimethylethyl)-2H-tetrazoyl]]methyl]phenyl]-propanoic acid, [Ac-(D,L)Phe(4-CH$_2$-tetrazole-tBu] (525 mg, 1.5 mmol). DCC (310 mg, 1.5 mmol) and HOBt (270 mg, 2 mmol) which were dissolved in 50 ml DMF/CH$_2$Cl$_2$ (1:1) by volume and allowed to react for 60 min at room temperature. At this point, the peptidyl-resin was dried under high vacuum to provide 1.7 g of Ac-(D,L)Phe(4-CH$_2$ tetrazole-tBu)-Met-Gly-Trp(For)-Met-Asp(OBZl)-Phe-BHA-resin. 1.7 g of the resin was cleaved by treatment with 5 ml of HF containing 2.0 ml of anisole, 1.0 ml of EDT and 15 ml of dimethylsulfide for 1 hour at 0° C. After evaporation to a low volume, fresh anhydrous HF (20 ml) was distilled into the reaction vessel for a second treatment for 2 hours at 0 C. After thorough evaporation, the resin was washed with 2 volumes of ethylacetate then triturated with 4×15 ml of 30% acetic acid, filtered and lyophilized to yield 456 mg of crude peptide. 80 mg of the crude peptide was purified by preparative HPLC as a (2.3×30) cm micro BONDAPACK C$_{18}$ column. The peptide was eluted with a linear gradient (4 h) of 5 to 65%. 0.022% TFA/CH$_3$CN of a flow rate of 8 ml/min. detection of 280 nm. The main peak was collected and lyophilized to yield 18 mg (20%) of Ac-(D,L)Phe(4-CH$_2$-tetrazole)-Met-Gly-Trp-Met-Asp-Phe-NH$_2$. This material was homogeneous by HPLC and gave the correct amino acid analysis and MS. Amino acid analysis Asp 1.00 (1); Gly 1.06(1); Met 1.80(2) Phe 1.00(1); Phe(4-CH$_2$tetrazole) 0.95 (1); Trp 0.70 (1); Empirical Formula: C$_{49}$H$_{61}$N$_{13}$O$_{10}$S$_2$ MW 1056.30.

EXAMPLE 61

Preparation of
Ac-(D)Phe(4-CH2-tetrazole)-Met-Gly-Trp-Met-Asp-Phe-NH$_2$ 2 mg of Ac-(D,L)-Phe(4-CH$_2$-tetrazole)-Met-Gly-Trp-Met-Asp-Phe-NH$_2$ obtained from Example 60 were dissolved in 0.5 mL of 0.2N NH$_4$OH and applied to (2.3×30 cm) micro Bondapak C-18 column from E.S. Industries. The column was previously equilibrated with 1% CH$_3$CN/0.01M NH$_4$OAc and eluted with a step gradient of 1-20% CH$_3$CN/0.01M NH$_4$OAc over 5 min at 8 mL/min, then 20-30% CH$_3$CN/0.01M NH$_4$OAc over 120 min at 8 mL/min. The 280 nm absorption of the column effluent was monitored. Two peaks were detected eluting at 51 min and 55 min. Fractions containing these peaks were pooled and lyophilized to 1 mg of white powder. Analysis by Glass Capillary Gas Chromatography shows that the compound eluting at 51 retention time contains the (D)-Phe(CH$_2$-tetrazole) enantiomer. The purity of this compound was also confirmed by analytical HPLC, amino acid analysis, UV and IR.

EXAMPLE 62

Preparation of
Ac-Phe(4-CH$_2$-tetrazole)-Met-Gly-Trp-Met-Asp-Phe-NH$_2$

From Example 61, the compound eluting at 55 min retention time was analyzed by Glass Capillary Gas Chromatography and shown to contain the (L)-Phe(4-CH$_2$-tetrazole) enantiomer. The purity of this compound was also determined by analytical HPLC, amino acid analysis, UV and IR.

EXAMPLE 63

Preparation of
Ac-(D,L)Phe(4-CH$_2$-tetrazole)-Nle-Gly-Trp-Nle-Asp-N-methyl-Phe-NH$_2$ 1 g (0.37 mmol) Boc-N-methyl-Phe-BHA resin was suspended and shaken in TFA/CH$_2$Cl$_2$ (1:1) by volume (3×40 mL) 10 min each time at room temperature to remove the Boc-group. The product was isolated by filtration and washed (3×50 mL each) with CH$_2$Cl$_2$, 8% DIEA in CH$_2$Cl$_2$ and CH$_2$Cl$_2$ to give the free base of N-methyl-Phe-BHA resin. This was subjected to sequential solid phase peptide synthesis using the DCC/HOBt procedure. At Step 16 the Boc-amino acid, DCC and HOBt were added with the corresponding reaction times as follows: Boc-Asp(OBzl)-OH (485 mg, 1.5 mmol), DCC (310 mg, 1.5 mmol) and HOBt (270 mg, 2 mmol) were dissolved in 20 mL 1:1 by volume DMF/CH$_2$Cl$_2$ and allowed to couple for 60 min at room temperature. Boc-Nle-OH (350 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Trp(For)-OH (500 mg, 1.5 mmol), DCC (310 mg, 1.5 mmol) and HOBt (270 mg, 2 mmol) were dissolved in 20 mL of DMF, and allowed to couple for 60 min at room temperature. Boc-Gly-OH (270 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Nle-OH (350 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. The compound of Example (17e) rac.-2-acetamido-3-[4-[[5-[2-(1,1-dimethylethyl)-2H-methyl]-tetrazoyl]]phenyl]propanoic acid (530 mg, 1.5 mmol), DCC (310 mg, 1.5 mmol) and HOBt (270 mg, 2 mmol) were dissolved in 30 mL of 1:1 by volume DMF (CH$_2$Cl$_2$) and allowed to couple for 60 min at room temperature. At this point the peptidyl-resin was dried under high vacuum to provide 1.7 g of Ac-(D,L)-Phe(4-CH$_2$-tetrazole-tBu)-Nle-Gly-Trp(For)-Nle-Asp(OBzl)-N-methyl-Phe-BHA resin. 1.7 g of the resin was cleaved by treatment with 5 mL of HF containing 2.0 mL of anisole, 1.0 mL of EDT and 15 mL of dimethylsulfide for 1 h at 0° C. After evaporation to a low volume, fresh anhydrous HF (20 mL) was distilled into the reaction vessel for a second treatment for 2 h at 0° C. After thorough evaporation, the resin was washed with 2 volumes of ethylacetate, then triturated with 4×15 mL of 30% acetic acid, filtered and lyophilized to yield 530 mg of crude peptide.

100 mg of the crude peptide was purified by preparative HPLC on a (2.3×30 cm) micro BONDAPACK C-18 column. The peptide was eluted with a linear gradient (4 h) of 5 to 65% 0.022% TFA/CH$_3$CN of a flow rate of 8 mL/min, detection at 280 nm. The main peak was collected and lyophilized to yield 10 mg (13.8%) of Ac-(D,L)-Phe(4-CH$_2$-tetrazole)-Nle-Gly-Trp-Nle-Asp-N-methyl-Phe-NH$_2$. This material was homogeneous by HPLC and gave the correct amino acid analysis and MS. Amino acid analysis: Asp, 0.98 (1); Gly, 0.96 (1); Nle, 2.00 (2); N-methyl-Phe, n.d.; Trp, n.d.; Phe(4-Ch$_2$-tetrazole), 0.90 (1): Empirical formula C$_{52}$H$_{67}$N$_{13}$O$_{10}$. M.W. 1034.12.

EXAMPLE 64

Preparation of
Ac-(D)-Phe(4-CH$_2$-tetrazole)-Nle-Gly-Trp-Nle-Asp-N-methyl-Phe-NH$_2$ 2 mg of Ac-(D,L)-Phe(4-CH$_2$-tetrazole)-Nle-Gly-Trp-Nle-Asp-N-methyl-Phe-NH$_2$ were dissolved in 0.5 mL of 0.2N NH$_4$OH and applied to (2.3×30 cm) micro BONDAPACK C-18 column from E. S. Industries. The column was previously equilibrated with 1% CH$_3$CN/0.01M NH$_4$OAc and eluted with a step gradient of 2-25% CH$_3$CN/0.01M NH$_4$OAc over 5 min at 8 mL/min, then 25-40% CH$_3$CN/0.01M NH$_4$OAc over 120 min at 8 mL/min. The 280 nm absorption of the column effluent was monitored. Two peaks were detected at 41 min and 44 min. Fractions containing these peaks were pooled and lyophilized to 1 mg of white powder. Analysis by Glass Capillary Gas Chromatography shows that the compound eluting at 41 min retention time contains the (D)-Phe(4-CH$_2$-tetrazole) enantiomer. The purity of this compound was also confirmed by analytical HPLC, amino acid analysis, UV and IR.

EXAMPLE 65

Preparation of
Ac-Phe(4CH2-tetrazole-Nle-Gly-Trp-Nle-Asp-N-methyl-Phe-NH$_2$

From Example 64, the compound eluting at 44 min retention time was analyzed by Glass Capillary Gas Chromatography and shown to contain the (L)-Phe(4-CH$_2$-tetrazole) enantiomer. The purity of this compound was also determined by analytical HPLC, amino acid analysis, UV and IR.

EXAMPLE 66

Desamino-Phe(4-CH2-tetrazole)-Nle-Gly-Trp-Nle-Asp-N-methyl-Phe-NH$_2$ 1.2 g (0.37 mmol) Boc-Nle-Gly-Trp(For)-Nle-Asp(OBzl)-N-methyl-Phe-BHA-resin obtained from Example 63 was deprotected with TFA/CH$_2$Cl$_2$ (1) by volume (Steps 1-15) using the Boc-protocol and coupled to the compound of Example 36, 4-[[2-(1,1-dimethylethyl)-2-tetrazol-5-yl]methyl]benzenepropanoic acid (500 mg, 1.5 mmol), DCC (310 mg, 1.5 mmol) and HOBt (270 mg, 2 mmol) which were dissolved in 50 mL of DMF/CH$_2$Cl$_2$ (1:1) by volume and allowed to react for 60 min at room temperature, then washed (Steps 17-27) and dried to yield 1.4 g Desamino-Phe(4-CH$_2$-tetrazole-tBu)-Nle-Gly-Trp(For)-Nle-Asp(OBzl)-N-methyl-PHe-BHA-resin. 1.4 g of the resin was cleaved by treatment with HF using the same condition as described in Example 63 to yield 400 mg of crude peptide. 100 mg of the crude peptide was purified by preparative HPLC on a (2.3×30 cm) micro BONDAPACK C-18 column. The peptide was eluted with a linear gradient (4 h) of 5 to 65% 0.022% TFA/CH$_3$CN of a flow rate of 8 mL/min, detection at 280 nm. The main peak was collected and lyophilized to yield 16 mg (17.7%) of Desamino-Phe (4-CH$_2$-tetrazole)-Nle-Gly-Trp-Nle-Asp-Phe-NH$_2$. This material was homogeneous by HPLC and gave the correct amino acid analysis and MS. Amino acid analysis: Asp, 1.01 (1); Gly, 1.00 (1); Nle, 1.90 (2); Trp, 0.80 (1); N-methyl-Phe, n.d. Empirical formula: C$_{50}$H$_{64}$N$_{12}$O$_9$. M.W. 977.15.

EXAMPLE 67

Desamino-Phe(4-tetrazole)-Met-Gly-Trp-Met-Asp-Phe-NH$_2$ 1.4 g (0.48 mmol) of Boc-Met-Gly-Trp(For)-Met-Asp(OBzl)-Phe-BHA-resin obtained from Example 53 was deprotected with TFA/CH$_2$Cl$_2$ (1:1) by volume (Steps 1-15) using the Boc-protocol and coupled to the compound of Example 41 4-[2-(1,1-dimethylethyl)-2H-tetrazol-5-yl]-benzenepropanoic acid (475 mg, 1.5 mmol), DCC (310 mg, 1.5 mmol) and HOBt (270 mg, 2 mmol) which were dissolved in 50 mL of DMF/CH$_2$Cl$_2$ (1:1) by volume and allowed to react for 60 min at room temperature, then washed (Steps 17-27) and dried to yield 1.52 g of Desamino-Phe(4-tetrazole-tBu)-Met-Gly-Trp(For)-Met-Asp(OBzl)-Phe-BHA-resin. 1.52 g of the resin was cleaved by treatment with HF using the same conditions as described in Example 63 to yield 340 mg of crude peptide. 100 mg of the crude peptide was purified by preparative HPLC on a (2.3×30 cm) micro BONDAPACK C-18 column. The peptide was eluted with a linear gradient (4 h) of 5 to 65% 0.022% TFA/CH$_3$CN of a flow rate of 8 mL/min, detection at 280 nm. The main peak was collected and lyophilized to yield 15 mg (10.8%) of Desamino-Phe(4-tetrazole)-Met-Gly-Trp-Met-Asp-Phe-NH$_2$. This material was homogeneous by HPLC and gave the correct amino acid analysis and MS. Amino acid analysis: Asp, 1.07 (1); Gly, 0.97 (1); Met, 2.00 (2); Phe, 1.10 (1); Trp, n.d. Empirical formula C$_{46}$H$_{56}$N$_{12}$O$_9$S$_2$. M.W. 985.16.

EXAMPLE 68

Preparation of
Desamino-Phe(4-tetrazole)-Lys-Gly-Trp-Met-Asp-N-methyl-Phe-NH$_2$ 1.1 g (0.33 mmol) of Fmoc-Lys-Gly-Trp-Met-Asp-N-methyl-Phe-BHA-resin obtained from Example 56 was deprotected with 20% piperidine/DMF (Steps 1-6) using the Fmoc protocol and coupled to the compound of Example 41 4-[2-(1,1-dimethylethyl)-2H-tetrazol-5yl]-benzenepropanoic acid tetrazole (475 mg, 1.5 mmol), DCC (310 mg, 1.5 mmol) and HOBt (270 mg, 2 mmol) which were dissolved in 50 mL of DMF/CH$_2$Cl$_2$ (1:1) by volume and allowed to react for 60 min at room temperature, then washed (Steps 8-16) and dried to yield 1.3 g of Desamino-Phe(4-tetrazole-tBu)-Lys-Gly-Trp-Met-Asp-N-methyl-Phe-BHA-resin. 1.3 g of the resin was cleaved by treatment with HF using the same conditions as described in Example 68 to yield 439 mg of crude peptide. 150 mg of the crude peptide was purified by preparative HPLC on a (2.3×30 cm) micro BONDAPACK C-18 column. The peptide was eluted with a linear gradient (4 h) of 5 to 65% 0.022% TFA/CH3CN of a flow rate of 8 mL/min, detection at 280 nm. The main peak was collected and lyophilzed to yield 15 mg (13.7%) of Desamino-Phe-(4-tetrazole)-Lys-Gly-Trp-Met-Asp-N-methyl-Phe-NH$_2$.

This material was homogeneous by HPLC and gave the correct amino acid analysis and MS. Amino acid analysis: Asp, 0.60 (1); Gly, 0.92 (1); Met, 1.00 (1); Lys, 0.60 (1); Trp, 0.90 (1); N-methyl-Phe, n.d. Empirical formula $C_{48}H_{59}N_{13}O_8S$. M.W. 978.17.

EXAMPLE 69

Preparation of Desamino-Phe(4-CH$_2$-COOH)-Met-Gly-Trp-Met-Asp-N-methyl-Phe-NH$_2$ 5 g of Fmoc-PAL-resin (substitution 0.38 mmol/g) was suspended and shaken in 20% piperidine/DMF (Steps 1-6) using the Fmoc protocol and coupled to Fmoc-N-methyl-Phe (2.4 g, 6 mmol) using DCC (1.25 g, 6 mmol) and HOBt (1.2 g, 9 mmol) which were dissolved in 100 mL DMF/CH$_2$Cl$_2$ (2:1) by volume and allowed to react for 12 h at room temperature, then washed (Steps 8-16) and dried to yield 5.5 g of Fmoc-N-methyl-Phe-PAL-resin. The substitution was determined by the Gisin method to be 0.34 mmol/g. A portion, 1 g (0.34 mmol) of the Fmoc-N-methyl-Phe-PAL-resin was subjected to sequential solid phase synthesis using the Fmoc-protocol. All couplings except the last residue were performed using DCC/HOBt procedure. At Step 7 the Fmoc-amino acid, DCC and HOBt were added with the corresponding reaction times as follows: Fmoc-Asp(OtBu)-OH (615 mg, 1.5 mmol), DCC (310 mg, 1.5 mmol) and HOBt (270 mg, 2 mmol), were dissolved in 20 mL of 1:1 by volume DMF/CH$_2$Cl$_2$, and allowed to couple for 60 min at room temperature. Fmoc-Met-OH (550 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Fmoc-Trp-OH (650 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Fmoc-Gly-OH (450 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Fmoc-Met-OH (550 mg, 1.5 mmol), DCC (310 mg, 1.5 mmol) and HOBt (270 mg, 2 mmol), were dissolved in 20 mL of 1:1 by volume DMF/CH$_2$Cl$_2$ and allowed to couple for 60 min at room temperature. At this point the Fmoc-Met-Gly-Trp-Met-Asp(OtBu) N-methyl-Phe-PAL-resin was suspended and shaken in 20 % piperidine/DMF (Steps 1-6) using the Fmoc-protocol and coupled to the compound of Example 26 N-hydroxysuccinyl 3-(4-carboxymethyl)phenylpropaonoate (610 mg, 2 mmol) which was dissolved in 20 mL DMF/CH$_2$Cl$_2$ (1:1) by volume and allowed to react for 6 h at room temperature, then washed (Steps 8-16) and dried to yield 1.40 g of Desamino-Phe(4-CH$_2$COOH)-Met-Gly-Trp-Met-Asp(OtBu)-N-methyl-Phe-PAL resin. This peptidyl-resin was suspended and shaken in 50 mL of TFA-/EDT/CH$_2$Cl$_2$ (14/1/5) by volume for 1 hour at room temperature, then the PAL resin was filtered off and washed with 20 mL of TFA/CH$_2$Cl$_2$ (1:1) by volume. The combined filtrates were evaporated to dryness, precipitated with ether, filtered off and dried to yield 268 mg of crude peptide. 135 mg of the crude peptide was purified by preparative HPLC on a (2.3×30 cm) micro Bondapak C-18 column. The peptide was eluted with a linear gradient of 5 to 65% of 0.022% TFA/CH$_3$CN at a flow rate of 8 mL/min, detection at 280 nm. The main peak was collected and lyophilized to yield 12 mg (7.2%) of Desamino-Phe(4-CH$_2$COOH)-Met-Gly-Trp-Met-Asp-N-methyl-Phe-NH$_2$. This material was homogeneous by HPLC and gave the correct amino acid analysis and MS. Amino acid analysis: Asp. 1.00 (1); Gly, 1.05 (1); Met, 1.80 (2); N-methyl-Phe, n.d.; Trp, n.d. Empirical formula: $C_{48}H_{60}N_8O_{11}S_2$. M.W. 989.15.

EXAMPLE 70

Preparation of Desamino-Phe(4-CH$_2$COOH)-Nle-Gly-Trp-Nle-Asp-N-methyl-Phe-NH$_2$ 1 g (0.34 mmol) of Fmoc-N-methyl-Phe-PAL-resin obtained from Example 69 was subjected to sequential solid phase synthesis using the Fmoc-protocol. All couplings except the last residue were performed using the DCC/HOBt procedure. At Step 7 the Fmoc-amino acid, DCC and HOBt were added with the corresponding reaction times as follows: Fmoc-Asp(OtBu)-OH (615 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Fmoc-Nle-OH (520 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Fmoc-Trp-OH (650 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Fmoc-Gly-OH (450 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Fmoc-Nle-OH (520 mg, 1.5 mmol), DCC (310 mg, 1.5 mmol) and HOBt (270 mg, 1.5 mmol) were dissolved in 20 mL of 1:1 by volume of DMF/CH$_2$Cl$_2$ and allowed to couple for 60 min at room temperature. At this point the Fmoc-Nle-Gly-Trp-Nle-Asp(OtBu)-N-methyl-Phe-PAL-resin was suspended and shaken in 20% piperidine/DMF (Steps 1-6) using the Fmoc protocol and coupled to the compound of Example 26 N-hydroxysuccinyl3-(4-carboxymethyl)-phenylpropaonoate (610 mg, 2 mmol) which was dissolved in 20 mL DMF/CH$_2$Cl$_2$ (1:1) by volume and allowed to react for 6 h at room temperature, then washed (Steps 8-16) and dried to yield 1.45 g of Desamino-Phe(4-CH$_2$COOH)-Nle-Gly-Trp-Nle-Asp-(OtBu)-N-methyl-Phe-PAL-resin. This peptidyl-resin was suspended and shaken in 50 mL of TFA-/EDT/CH$_2$Cl$_2$ (14/1/5) by volume for 1 h at room temperature, then the PAL resin was filtered off and washed with 20 mL TFA (CH$_2$Cl$_2$ (1:1) by volume. The combined filtrates were evaporated to dryness, precipitated with ether, filtered off and dried to yield 240 mg of crude peptide.

120 mg of the crude peptide was purified by preparative HPLC on a (2.3×30 cm) micro BONDAPACK C-18 column. The peptide was eluted with a linear gradient of 5 to 65% of 0.022% TFA/CH$_3$CN at a flow rate of 8 mL/min, detection at 280 nm. The main peak was collected and lyophilized to yield 10 mg (6.2%) of Desamino-Phe(4-CH$_2$COOH)-Nle-Gly-Trp-Nle-Asp-N-methyl-Phe-NH$_2$. This material was homogeneous by HPLC and gave the correct amino acid analysis and MS. Amino acid analysis: Asp, 0.96 (1); Gly, 0.93 (1);

Nle, 2.00 (2); N-methyl-Phe, n.d. Empirical formula: $C_{50}H_{64}N_8O_{11}$. M.W. 953.11.

EXAMPLE 71

Preparation of Desamino-Phe(4CH$_2$COOH)-Nle-(D)Ala-Trp-Nle-Asp-N-methyl-Phe-NH$_2$ 1.25 g (0.43 mmol) of Fmoc-Trp-Nle-Asp(OtBu)-N-methyl-Phe-PAL-resin obtained from Example 70 was subjected to sequential solid phase synthesis using the Fmoc protocol. All couplings except the last residue were performed using the DCC/HOBt procedure. At Step 7 the Fmoc-amino acid, DCC and HOBt were added with the corresponding reaction times as follows: Fmoc(D)-Ala-OH (480 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Fmoc-Nle-OH (520 mg, 1.5 mmol), DCC (310 mg, 1.5 mmol) and HOBt (270 mg, 2 mmol) were dissolved in 20 mL of 1:1 by volume of DMF/CH$_2$Cl$_2$ and allowed to couple for 60 min at room temperature. At this point the Fmoc-Nle-(D)Ala-Trp-Nle-Asp(OtBu)-N-methy-Phe-PAL-resin was suspended and shaken in 20% piperidine/DMF (Steps 1–6) using the Fmoc protocol and coupled to the compound of Example 26 N-hydroxysuccinyl 3-(4-carboxymethyl)phenylpropaonoate (610 mg, 2 mmol) which was dissolved in 20 mL DMF/CH$_2$Cl$_2$ (1:1) by volume and allowed to react for 6 h at room temperature, then washed (Steps 6–16) and dried to yield 1.5 g of Desamino-Phe(4-CH$_2$COOH)-Nle-(D)Ala-Trp-Nle-Asp(OtBu)-N-methyl-Phe-PAL-resin. This peptidyl-resin was suspended and shaken in 50 mL of TFA/EDT/CH$_2$Cl$_2$ (14/1/5) by volume for 1 h at room temperature, then the resin was filtered off and washed with 20 mL TFA/CH$_2$Cl$_2$ (1:1) by volume. The combined filtrates were evaporated to dryness, precipitated with ether, filtered off and dried to yield 300 mg of crude peptide.

150 mg of the crude peptide was purified by preparative HPLC on a (2.3×30 cm) micro BONDAPACK C-18 column. The peptide was eluted with a linear gradient of 5 to 65% of 0.022% TFA/CH$_3$CN at a flow rate of 8 mL/min, detection at 280 nm. The main peak was collected and lyophilized to yield 20 (12.1%) mg of Desamino-Phe(4-CH$_2$COOH)-Nle-(D)Ala-Trp-Nle-Asp-N-methyl-Phe-NH$_2$. This material was homogeneous by HPLC and gave the correct amino acid analysis and MS. Amino acid analysis: Asp, 0.95 (1); Ala, 1.03 (1); Nle, 2.02 (2); N-methyl-Phe, n.d.; Trp, n.d. Empirical formula: $C_{51}H_{66}N_8O_{11}$. M.W. 967.13.

EXAMPLE 72

In Vitro Receptor Binding Assay

Frozen bovine striatum (approx. 5 g) or fresh rat pancreas (approx. 5 g) cleaned of fat and extraneous tissue were homogenized in HEPES buffer #1 (10 mM HEPES+130 nM NaCl+5 mM MgCl$_2$, pH 7.4) using 35 parts buffer per 1 part tissue on a wet weight/volume basis (approx. 175 mL). The tissue was homogenized 2× for approx. 15 sec. at 0° C. using a Polytron homogenizer at a setting of 6. The tissue was isolated by centrifugation at 48,000×g for 10 min at 0° C. The resulting tissue pellet was resuspended in HEPES buffer #2 (10 mM HEPES+130 mM NaCl+5 mM MgCl$_2$+1 mg/L phenylmethanesulfonyl fluoride (PMSF)+200 mg/L Bacitracin): 1 part striatal tissue (original wet weight) oer 80 parts buffer and 1 part pancreas tissue (original wet weight) per 500 to 1000 parts buffer.

Incubation was initiated by combining various concentrations of native CCK-8 or peptides of the invention with $^3$H-CCK-8-(SO$_3$H) (final conc.=0.15 nM) and tissue homogenate (striatum approximately. 0.26 mg protein in 2 mL final volume; pancreas approximately 0.100 mg protein in 1 mL final volume). Samples were incubated for 30 min at 25° C. and the incubation terminated by pouring the mixture onto a pre-wetted Whatman GF/B filter on a Sandbeck Vacuum Filtration Manifold. The incubation tubes were washed with 2×3 mL of ice-cold HEPES Buffer #2 and the wash filtered through the GF/B filter. The filter was air dried for 10 min and then placed in a scintillation vial with 12 mL of DuPont/NEN AQUASOL scintillation cocktail. The vials were shaken overnight and then counted using a liquid scintillation spectrometer. Non-specific binding was determined in the presence of 1 micromolar native CCK-8 and subtracted from all samples to determine specific binding. The concentration of peptide necessary to inhibit 50% of total specific $^3$H-CCK-8-(SO$_3$H) binding (IC$_{50}$ value) was determined by log-probit analysis. The results are summarized in Table I.

EXAMPLE 73

Two-Meal Feeding Assay

Male Spraque-Dawley (CD) rats weighing 180–200 grams (Charles River Breeding Laboratories) were acclimated to a 12 h light/dark cycle (6 a.m. to 6 p.m.) in a room kept at 22° C. They were subsequently fasted for two days, weighed, placed in individual cages, and a four-day period of meal training was begun. During this time the rats were given ground laboratory chow (Purina LAB CHOW) in jars for one hour from 9:00 a.m. until 10:00 a.m., the jars were removed from 10:00 a.m. to 12:00 p.m., and placed back in the cages from 12:00 until 1:00 p.m. Under this '1-2-1' meal feeding regime, most rats learn to eat approximately as much per day during the two hours they have access to food as rats which have food ad libitum over the entire 24-hour day. On the fourth day, the rats were weighed again, and any which lost more than five grams body weight were excluded from the test. The animals were then distributed into experimental (n=5 to 6) and control groups (n=6–12), but not matched for body weight.

Peptides of the invention were suspended either in saline, if soluble, or in 0.5% DMSO/saline, if insoluble, at concentrations of 0 to 320 µg/mL/kg body weight and were administered intraperitoneally 15 min before the first meal on day 5 of meal feeding. The rats were then given their meals as they had been during the previous four days, and the food cups were weighed both before and after each meal to determine food consumption. Food intake was expressed as a mean and standard error of the mean in percent of control values for the various groups. The treated groups were compared to the control groups by t-test analysis. The results are summarized in Table 1.

While the invention has been described in connection with the preferred embodiment, it is not intended to limit the scope of the invention to the particular form set forth, but, on the contrary, it is intended to cover such alternatives, modifications, and equivalents as may be included within the spirit and scope of the appended claims.

TABLE I

| Peptides | Ex. No. | Bovine Striatum (nM) | Rat Pancreas (nM) | Dose Microgram/kg | Food Intake 1st Meal % of Control | Food Intake 2nd Meal % of Control |
|---|---|---|---|---|---|---|
| Asp—Tyr(SO$_3$H)—Met—Gly—Trp—Met—Asp—Phe—NH$_2$ | CCK-8 | 1–3.2 | 1–4.6 | 32 | 27 ± 17*** | 149 ± 6*** |
| Ac—(D,L)Phe(3-COOH)—Met—Gly—Trp—Met—Asp—Phe—NH$_2$ | 42 | 32 | 128 | 32 | 125 ± 12 | 98 ± 9 |
| Ac—(D,L)Phe(4-COOH)—Met—Gly—Trp—Met—Asp—Phe—NH$_2$ | 43 | 34 | 62 | 320 | 98 ± 14 | 110 ± 12 |
| | | | | 320 | 43 ± 11*** | 118 ± 13 |
| | | | | 1060 | 41 ± 11*** | 113 ± 8 |
| Ac—(D)Phe(4-COOH)—Met—Gly—Trp—Met—Asp—Phe—NH$_2$ | 44 | 68 | 210 | 32 | 89 ± 6 | 123 ± 9 |
| | | | | 320 | 85 ± 4 | 146 ± 6* |
| Ac—Phe(4-COOH)—Met—Gly—Trp—Met—Asp—Phe—NH$_2$ | 45 | 62 | 30 | 32 | 79 ± 12 | 140 ± 6* |
| | | | | 320 | 12 ± 6** | 165 ± 8** |
| Ac—(D,L)Phe(4-CH$_2$COOH)—Met—Gly—Trp—Met—Asp—Phe—NH$_2$ | 46 | 47 | 3.6 | 3 | 97 ± 15 | 98 ± 6 |
| | | | | 16 | 26 ± 5*** | 157 ± 18** |
| | | | | 32 | 12 ± 4*** | 133 ± 10** |
| | | | | 320 | 1 ± 1*** | 142 ± 6** |
| Ac—(D)Phe(4-CH$_2$COOH)—Met—Gly—Trp—Met—Asp—Phe—NH$_2$ | 47 | 145 | 21 | 3 | 95 ± 4 | 100 ± 10 |
| | | | | 16 | 53 ± 5*** | 172 ± 6** |
| | | | | 320 | 31 ± 19** | 141 ± 12* |
| Ac—Phe(4-CH$_2$COOH)—Met—Gly—Trp—Met—Asp—Phe—NH$_2$ | 48 | 54 | 2.6 | 3 | 76 ± 6* | 139 ± 16 |
| | | | | 16 | 38 ± 5** | 179 ± 20* |
| | | | | 320 | 1 ± 0*** | 116 ± 14 |
| Ac—(D)Phe(4-CH$_2$COOC$_2$H$_5$)—Met—Gly—Trp—Met—Asp(COOC$_2$H$_5$)—Phe—NH$_2$ | 49 | 10000 | 1000 | 1 | 93 ± 3 | 98 ± 15 |
| | | | | 3 | 71 ± 8** | 165 ± 14** |
| | | | | 32 | 12 ± 6** | 228 ± 16*** |
| | | | | 320 | 1 ± 0*** | 109 ± 5 |
| Ac—Phe(4-CH$_2$COCH$_3$)—Met—Gly—Trp—Met—Asp(COOC$_2$H$_5$)—Phe—NH$_2$ | 50 | 10000 | 3600 | 3 | 97 ± 3 | 112 ± 8 |
| | | | | 32 | 66 ± 6* | 138 ± 5* |
| | | | | 96 | 50 ± 14** | 169 ± 22** |
| | | | | 320 | 16 ± 6*** | 165 ± 8*** |
| Ac—Phe(4-CH$_2$CH$_2$COOH)—Met—Gly—Trp—Met—Asp—Phe—NH$_2$ | 51 | 620 | 390 | 320 | 103 ± 5 | 114 ± 7 |
| Ac—(D,L)Phe(4-CF$_2$COOH)—Met—Gly—Trp—Met—Asp—Phe—NH$_2$ | 52 | 66 | 81 | 32 | 54 ± 8** | 186 ± 3*** |
| | | | | 100 | 10 ± 2** | 201 ± 3*** |
| Ac—(D,L)Phe(4-tetrazole)—Met—Gly—Trp—Met—Asp—Phe—NH$_2$ | 53 | 1.6 | 22 | 16 | 49 ± 11** | 144 ± 8** |
| | | | | 32 | 28 ± 9*** | 146 ± 12** |
| | | | | 320 | 14 ± 5*** | 131 ± 8* |
| Ac—(D)Phe(4-tetrazole)—Met—Gly—Trp—Met—Asp—Phe—NH$_2$ | 54 | 50 | 120 | 3 | 86 ± 16 | 140 ± 25 |
| | | | | 16 | 89 ± 6 | 145 ± 12 |
| Ac—Phe(4-tetrazole)—Met—Gly—Trp—Met—Asp—Phe—NH$_2$ | 55 | 0.51 | 3.0 | 3 | 70 ± 10 | 156 ± 8* |
| | | | | 16 | 32 ± 10*** | 191 ± 10** |
| Ac—(D,L)Phe(4-CH$_2$COOH)—Lys—Gly—Trp—Met—Asp—N—methyl—Phe—NH$_2$ | 56 | 10000 | 4650 | 32 | 89 ± 7 | 98 ± 9 |
| | | | | 320 | 80 ± 3** | 121 ± 2 |
| Ac—(D,L)Phe(4-tetrazole)—Lys—Gly—Trp—Met—Asp—N—methyl—Phe—NH$_2$ | 57 | 580 | 1100 | 32 | 75 ± 6** | 160 ± 14*** |
| | | | | 320 | 36 ± 3*** | 148 ± 6* |
| Ac—(D,L)Phe(3-CH$_2$COOH)—Met—Gly—Trp—Met—Asp—Phe—NH$_2$ | 58 | 53 | 23 | 32 | 40 ± 9*** | 169 ± 11*** |
| | | | | 320 | 0 ± 0*** | 163 + 13*** |
| Des amino Phe(4-CH$_2$COOH)—Met—Gly—Trp—Met—Asp—Phe—NH$_2$ | 59 | 22 | 57 | 3 | 59 ± 5** | 197 ± 21** |
| | | | | 32 | 10 ± 4*** | 121 ± 14 |
| Ac—(D,L)Phe(4-CH$_2$-tetrazole)—Met—Gly—Trp—Met—Asp—Phe—NH$_2$ | 60 | 340 | 730 | 32 | 63 ± 9** | 140 ± 15 |

TABLE I-continued

| Peptides | Ex. No. | Bovine Striatum (nM) | Rat Pancreas (nM) | Dose Microgram/kg | Food Intake 1st Meal % of Control | Food Intake 2nd Meal % of Control |
|---|---|---|---|---|---|---|
| Ac—(D)Phe(4-CH$_2$-tetrazole)—Met—Gly—Trp—Met—Asp—Phe—NH$_2$ | 61 | 62 | 380 | 320 | 12 ± 4*** | 165 ± 19 |
|  |  |  |  | 32 | 80 ± 6* | 119 ± 28 |
|  |  |  |  | 100 | 58 ± 6*** | 159 ± 9* |
|  |  |  |  | 320 | 47 ± 13*** | 170 ± 21* |
| Ac—Phe(4-CH$_2$-tetrazole)—Met—Gly—Trp—Met—Asp—Phe—NH$_2$ | 62 | 18 | 67 | 3 | 85 ± 6* | 118 ± 9 |
|  |  |  |  | 10 | 65 ± 4*** | 129 ± 9*** |
|  |  |  |  | 32 | 25 ± 4*** | 170 ± 12** |
|  |  |  |  | 100 | 16 ± 3*** | 179 ± 14** |
| Ac—(D,L)Phe(4-CH$_2$-tetrazole)—Nle—Gly—Trp—Nle—Asp—N—methyl—Phe—NH$_2$ | 63 | 260 | 640 | 32 | 53 ± 10** | 171 ± 3*** |
|  |  |  |  | 320 | 19 ± 5*** | 141 ± 17 |
| Ac—(D)Phe(4-CH$_2$-tetrazole)—Nle—Gly—Trp—Nle—Asp—N—methyl—Phe—NH$_2$ | 64 | 160 | 800 | 10 | 112 ± 10 | 102 ± 9 |
|  |  |  |  | 32 | 79 ± 5* | 148 ± 12* |
|  |  |  |  | 100 | 56 ± 6*** | 173 ± 5*** |
|  |  |  |  | 320 | 21 ± 6*** | 207 ± 20*** |
| Ac—Phe(4-CH$_2$-tetrazole)—Nle—Gly—Trp—Nle—Asp—N—Methyl—Phe—NH$_2$ | 65 | 69 | 260 | 10 | 86 ± 11 | 133 ± 11* |
|  |  |  |  | 100 | 30 ± 4*** | 164 ± 9*** |
| Des amino Phe(4-CH$_2$-tetrazole)—Nle—Gly—Trp—Mle—Asp—N—methyl—Phe—NH$_2$ | 66 | 160 | 710 | 3 | 94 ± 9 | 109 ± 16 |
|  |  |  |  | 32 | 68 ± 6* | 179 ± 16** |
|  |  |  |  | 100 | 56 ± 5** | 205 ± 7*** |
|  |  |  |  | 320 | 34 ± 5*** | 177 ± 14*** |
| Des amino Phe(4-tetrazole)—Met—Gly—Trp—Met—Asp—Phe—NH$_2$ | 67 | 5.1 | 35 | 3 | 99 ± 9 | 116 ± 6 |
|  |  |  |  | 32 | 26 ± 4*** | 204 ± 9*** |
| Des amino Phe(4-tetrazole)—Lys—Gly—Trp—Met—Asp—N—Methyl—Phe—NH$_2$ | 68 | 1400 | 2900 | 32 | 77 ± 8* | 165 ± 18** |
|  |  |  |  | 320 | 24 ± 3*** | 177 ± 14*** |
| Des amino-Phe(4-CH$_2$—COOH)—Met—Gly—Trp—Met—Asp—N—methyl—Phe—NH$_2$ | 69 | 3.2 | 1.8 | 1 | 99 ± 7 | 106 ± 8 |
|  |  |  |  | 3 | 99 ± 9 | 127 ± 10 |
|  |  |  |  | 10 | 53 ± 11* | 163 ± 10*** |
|  |  |  |  | 32 | 16 ± 5*** | 157 ± 13* |
| Des amino-Phe(4-CH$_2$—COOH)—Nle—Gly—Trp—Nle—Asp—N—Methyl—Phe—NH$_2$ | 70 | 200 | 330 | 3 | 78 ± 6* | 151 ± 16* |
|  |  |  |  | 10 | 65 ± 7** | 165 ± 7*** |
|  |  |  |  | 32 | 27 ± 6*** | 140 ± 12** |
|  |  |  |  | 320 | 9 ± 4*** | 113 ± 9 |
| Des amino-Phe(4-CH$_2$—COOH)—Nle(D)Ala—Trp—Nle—Asp—N—Methyl—Phe—NH$_2$ | 71 | 1400 | 1800 | 36 | 93 ± 9 | 109 ± 6* |
|  |  |  |  | 320 | 105 ± 4 | 89 ± 12* |

Values significantly different than their respective controls.
*p ≦ 0.001, p = 0.01, *p ≦ 0.05

We claim:
1. Ac-(D,L)-Phe(4-COOH)-Met-Gly-Trp-Met-Asp-Phe-NH$_2$.
2. Ac-(D)-Phe(4-COOH)-Met-Gly-Trp-Met-Asp-Phe-NH$_2$.
3. Ac-Phe(4-COOH)-Met-Gly-Trp-Met-Asp-Phe-NH$_2$.
4. Ac-(D,L)-Phe(4-CH$_2$COOH)-Met-Gly-Trp-Met-Asp-Phe-NH$_2$.
5. Ac-(D)-Phe(4-CH$_2$COOH)-Met-Gly-Trp-Met-Asp-Phe-NH$_2$.
6. Ac-Phe(4-CH$_2$COOH)-Met-Gly-Trp-Met-Asp-Phe-NH$_2$.
7. Desamino-Phe(4-CH$_2$COOH)-Met-Gly-Trp-Met-Asp-Phe-NH$_2$.
8. Desamino-Phe(4-CH$_2$COOH)-Nle-Gly-Trp-Nle-Asp-N-methyl-Phe-NH$_2$.
9. Desamino-Phe(4-CH$_2$COOH)-Nle-D-Ala-Trp-Nle-Asp-N-methyl-Phe-NH$_2$.
10. Ac-(D,L)-Phe(4-CF$_2$COOH)-Met-Gly-Trp-Met-Asp-Phe-NH$_2$.
11. Ac-(D)-Phe(4-CH$_2$COOC$_2$H$_5$)-Met-Gly-Trp-Met-Asp-(COOC$_2$H$_5$)-Phe-NH$_2$.
12. Ac-Phe(4-CH$_2$COOC$_2$H$_5$)-Met-Gly-Trp-Met-Asp-(COOC$_2$H$_5$)-Phe-NH$_2$.
13. Ac-Phe(4-CH$_2$CH$_2$COOH)-Met-Gly-Trp-Met-Asp-Phe-NH$_2$.
14. Ac-(D,L)-Phe(3-COOH)-Met-Gly-Trp-Met-Asp-Phe-NH$_2$.
15. Ac-(D,L)-Phe(3-CH$_2$COOH)-Met-Gly-Trp-Met-Asp-Phe-NH$_2$.
16. Ac-(D,L)-Phe(4-tetrazole)-Met-Gly-Trp-Met-Asp-Phe-NH$_2$.
17. Ac-(D)-Phe(4-tetrazole)-Met-Gly-Trp-Met-Asp-Phe-NH$_2$.
18. Ac-Phe(4-tetrazole)-Met-Gly-Trp-Met-Asp-Phe-NH$_2$.
19. Desamino-Phe(4-tetrazole)-Met-Gly-Trp-Met-Asp-Phe-NH$_2$.
20. Ac-(D,L)-Phe(4-CH$_2$-tetrazole)-Met-Gly-Trp-Met-Asp-Phe-NH$_2$.
21. Ac-(D)-Phe(4-CH$_2$-tetrazole)-Met-Gly-Trp-Met-Asp-Phe-NH$_2$.
22. Ac-(D,L)-Phe(4-CH$_2$-tetrazole)-Nle-Gly-Trp-Nle-Asp-N-methyl-Phe-NH$_2$.
23. Ac-(D)-Phe(4-CH$_2$-tetrazole)-Nle-Gly-Trp-Nle-Asp-N-methyl-Phe-NH$_2$.
24. Ac-Phe(4-CH$_2$-tetrazole)-Nle-Gly-Trp-Nle-Asp-N-methyl-Phe-NH$_2$.
25. Desamino-Phe(4-CH$_2$-tetrazole)-Nle-Gly-Trp-Nle-Asp-N-methyl-Phe-NH$_2$.
26. Desamino-Phe(4-CH$_2$-tetrazole)-Nle-(D)Ala-Trp-Nle-Asp-N-methyl-Phe-NH$_2$.
27. Ac-Phe(4-CH$_2$-tetrazole)-Met-Gly-Trp-Met-Asp-Phe-NH$_2$.
28. A method for suppressing appetite in subjects by administering an appetite supressing efective amount of a compound selected from the group consisting of:

Ac—(D,L)—Phe(3-COOH)—Met—Gly—Trp—Met—Asp—Phe—NH
Ac—(D,L)=Phe(4-COOH)—Met—Gly—Trp—Met—Asp—Phe—NH$_2$
Ac—(D)—Phe(4-COOH)—Met—Gly—Trp—Met—Asp—Phe—NH$_2$
Ac—Phe(4-COOH)—Met—Gly—Trp—Met—Asp—Phe—NH$_2$
Ac—(D,L)=Phe(4-CH$_2$COOH)—Met—Gly—Trp—Met—Asp—Phe—NH$_2$
Ac—(D)=Phe(4-CH$_2$COOH)—Met—Gly—Trp—Met—Asp—Phe—NH$_2$
Ac—Phe(4-CH$_2$COOH)—Met—Gly—Trp—Met—Asp—Phe—NH$_2$
Ac—(D)—Phe(4-CH$_2$COOC$_2$H$_5$)—Met—Gly—Trp—Met—Asp—(COOC$_2$H$_5$)—Phe—NH$_2$
Ac—Phe(4-CH$_2$COOC$_2$H$_5$)—Met—Gly—Trp—Met—Asp—(COOC$_2$H$_5$)—Phe—NH$_2$
Ac—Phe(4-CH$_2$CH$_2$COOH)—Met—Gly—Trp—Met—Asp—Phe—NH$_2$
Ac—(D,L)=Phe(4-CF$_2$COOH)—Met—Gly—Trp—Met—Asp—Phe—NH$_2$
Ac—(D,L)=Phe(4-tetrazole)—Met—Gly—Trp—Met—Asp—Phe—NH$_2$
Ac—(D)=Phe(4-tetrazole)—Met—Gly—Trp—Met—Asp—Phe—NH$_2$
Ac—Phe(4-tetrazole)—Met—Gly—Trp—Met—Asp—Phe—NH$_2$
Desamino=Phe(4-CH$_2$COOH)—Met—Gly—Trp—Met—Asp—Phe—NH$_2$
Ac—(D,L)—Phe(3-CH$_2$COOH)—Met—Gly—Trp—Met—Asp—Phe—NH$_2$
Ac—(D,L)=Phe(4-CH$_2$—tetrazole)—Met—Gly—Trp—Met—Asp—Phe—NH$_2$
Desamino=Phe(4-CH$_2$COOH)—Nle—Gly—Trp—Nle—Asp—N—methyl—Phe—NH$_2$
Desamino=Phe(4-CH$_2$COOH)—Nle—(D)—Ala—Trp—Nle—Asp—N—methyl—Phe—NH$_2$
Desamino=Phe(4-tetrazole)—Met—Gly—Trp—Met—Asp—Phe—NH$_2$
Ac—(D)=Phe(4-CH$_2$—tetrazole)—Met—Gly—Trp—Met—Asp—Phe—NH$_2$
Ac—Phe(4-CH$_2$—tetrazole)—Met—Gly—Trp—Met—Asp—Phe—NH$_2$
Ac—(D,L)=Phe(4-CH$_2$—tetrazole)—Nle—Gly—Trp—Nle—Asp—N—methyl—Phe—NH$_2$
Ac—Phe(4-CH$_2$—tetrazole)—Nle—Gly—Trp—Nle—Asp—N—methyl—Phe—NH$_2$ and
Desamino—Phe(4-CH$_2$—tetrazole)—Nle—Gly—Trp—Nle—Asp—N—methyl—Phe—NH$_2$.

29. The method of claim 28 wherein the analog is administered intranasally.
30. The method of claim 28 wherein the analog is administered parenterally.

* * * * *

UNITED STATES PATENT AND TRADEMARK OFFICE
CERTIFICATE OF CORRECTION

PATENT NO. : 5,182,263

DATED : January 26, 1993

INVENTOR(S) : Waleed Danho, Jefferson Tilley, Joseph Triscari and Rolf Wagner

It is certified that error appears in the above-identified patent and that said Letters Patent is hereby corrected as shown below:

In claim 28, column 58, line 10, "Ac-(D,L)-Phe(3-COOH)-Met-Gly-Trp-Met-Asp-Phe-NH" should be -- Ac-(D,L)-Phe(3-COOH)-Met-Gly-Trp-Met-Asp-Phe-NH$_2$ --

Signed and Sealed this

Fifth Day of April, 1994

BRUCE LEHMAN

Attest:

Attesting Officer

Commissioner of Patents and Trademarks